US012558423B2

(12) United States Patent
Kameoka et al.

(10) Patent No.: US 12,558,423 B2
(45) Date of Patent: Feb. 24, 2026

(54) ANTIBODY-CONTAINING FORMULATION

(71) Applicant: Chugai Seiyaku Kabushiki Kaisha, Tokyo (JP)

(72) Inventors: Daisuke Kameoka, Tokyo (JP); Masaya Yasutake, Tokyo (JP); Masakazu Fukuda, Tokyo (JP); Atsushi Watanabe, Tokyo (JP); Tomoyuki Igawa, Tokyo (JP); Chifumi Imai, Tokyo (JP); Akira Hayasaka, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 225 days.

(21) Appl. No.: 17/926,313

(22) PCT Filed: May 28, 2021

(86) PCT No.: PCT/JP2021/020337
§ 371 (c)(1),
(2) Date: Nov. 18, 2022

(87) PCT Pub. No.: WO2021/241720
PCT Pub. Date: Dec. 2, 2021

(65) Prior Publication Data
US 2023/0210991 A1       Jul. 6, 2023

(30) Foreign Application Priority Data

May 29, 2020   (JP) ................................. 2020-094716

(51) Int. Cl.
| | |
|---|---|
| A61K 39/395 | (2006.01) |
| A61K 9/08 | (2006.01) |
| A61K 9/19 | (2006.01) |
| A61K 47/10 | (2017.01) |
| A61K 47/18 | (2017.01) |
| A61K 47/22 | (2006.01) |
| C07K 16/28 | (2006.01) |
| A61K 39/00 | (2006.01) |

(52) U.S. Cl.
CPC .......... *A61K 39/39591* (2013.01); *A61K 9/08* (2013.01); *A61K 9/19* (2013.01); *A61K 47/10* (2013.01); *A61K 47/183* (2013.01); *A61K 47/22* (2013.01); *C07K 16/2866* (2013.01); *A61K 2039/54* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,126,250 A | 6/1992 | McDonough et al. | |
| 5,670,373 A | 9/1997 | Kishimoto | |
| 5,817,790 A | 10/1998 | Tsuchiya et al. | |
| 6,309,636 B1 | 10/2001 | do Couto et al. | |
| 6,723,319 B1 | 4/2004 | Ito et al. | |
| 6,884,879 B1 | 4/2005 | Baca et al. | |
| 7,479,543 B2 | 1/2009 | Tsuchiya et al. | |
| 8,217,147 B2 | 7/2012 | Stavenhagen et al. | |
| 8,562,991 B2 | 10/2013 | Igawa et al. | |
| 9,688,762 B2 * | 6/2017 | Igawa ..................... A61P 37/00 |
| 10,022,319 B2 | 7/2018 | Igawa et al. | |
| 10,662,245 B2 | 5/2020 | Igawa et al. | |
| 10,774,148 B2 | 9/2020 | Kakehi et al. | |
| 11,612,562 B2 * | 3/2023 | Igawa ................... A61K 47/12 |
| | | | 530/390.5 |
| 2001/0001663 A1 | 5/2001 | Kishimoto et al. | |
| 2001/0051154 A1 | 12/2001 | Roemisch et al. | |
| 2001/0055617 A1 | 12/2001 | Mattern et al. | |
| 2002/0187150 A1 | 12/2002 | Mihara et al. | |
| 2003/0224397 A1 | 12/2003 | Lowman et al. | |
| 2004/0071706 A1 | 4/2004 | Ito et al. | |
| 2004/0197324 A1 | 10/2004 | Liu et al. | |
| 2005/0074821 A1 | 4/2005 | Wild et al. | |
| 2005/0118163 A1 | 6/2005 | Mizushima et al. | |
| 2005/0142635 A1 | 6/2005 | Tsuchiya et al. | |
| 2005/0214278 A1 | 9/2005 | Kakuta et al. | |
| 2005/0261229 A1 | 11/2005 | Gillies et al. | |

(Continued)

FOREIGN PATENT DOCUMENTS

| | | |
|---|---|---|
| AR | 068564 | 11/2009 |
| BR | PI0415230 | 12/2006 |

(Continued)

OTHER PUBLICATIONS

U.S. Appl. No. 18/729,273, filed Jul. 16, 2024, Ozawa et al.
U.S. Appl. No. 18/820,608, filed Aug. 30, 2024, Kakehi et al.
U.S. Appl. No. 12/680,087, filed Jan. 3, 2011, Igawa et al.
U.S. Appl. No. 12/680,112, filed Jun. 23, 2010, Igawa et al.
U.S. Appl. No. 13/522,848, filed Jun. 15, 2012, Igawa et al.
U.S. Appl. No. 13/524,528, filed Jun. 15, 2012, Igawa et al.
U.S. Appl. No. 13/959,489, filed Aug. 5, 2013, Igawa et al.
U.S. Appl. No. 14/520,423, filed Oct. 22, 2014, Igawa et al.
U.S. Appl. No. 15/263,617, filed Sep. 13, 2016, Igawa et al.
U.S. Appl. No. 15/553,609, filed Aug. 25, 2017, Kakehi et al.
U.S. Appl. No. 16/008,486, filed Jun. 14, 2018, Igawa et al.
U.S. Appl. No. 16/041,976, filed Jul. 23, 2018, Igawa et al.
U.S. Appl. No. 16/838,415, filed Apr. 2, 2020, Igawa et al.

(Continued)

*Primary Examiner* — Yunsoo Kim
(74) *Attorney, Agent, or Firm* — Fish & Richardson P.C.

(57) ABSTRACT

In one non-limiting embodiment, the present disclosure is an antibody-containing formulation comprising an anti-IL-6 receptor antibody as an active ingredient, and contains histidine-aspartate buffer or histidine-glutamate buffer, Poloxamer 188, and arginine, and has a pH of 5.5 to 6.6. In one non-limiting embodiment, the present disclosure is a method of stabilizing an antibody-containing solution, a method of suppressing antibody association (e.g., dimerization), and a method of suppressing the generation of insoluble particles, wherein L-aspartic acid or L-glutamic acid, and optionally, Poloxamer 188 are added.

26 Claims, No Drawings

Specification includes a Sequence Listing.

(56)  References Cited

U.S. PATENT DOCUMENTS

| | | |
|---|---|---|
| 2006/0194280 A1 | 8/2006 | Dillon et al. |
| 2006/0240012 A1 | 10/2006 | Sugimura et al. |
| 2006/0292147 A1 | 12/2006 | Yoshizaki et al. |
| 2007/0036785 A1 | 2/2007 | Kishimoto et al. |
| 2007/0184050 A1 | 8/2007 | Ishikawa et al. |
| 2007/0212346 A1 | 9/2007 | Igawa et al. |
| 2007/0280945 A1 | 12/2007 | Stevens et al. |
| 2008/0071063 A1 | 3/2008 | Allan et al. |
| 2008/0145367 A1 | 6/2008 | Bove et al. |
| 2009/0263392 A1 | 10/2009 | Igawa et al. |
| 2009/0269335 A1 | 10/2009 | Nakashima et al. |
| 2009/0291076 A1 | 11/2009 | Morichika et al. |
| 2009/0324589 A1 | 12/2009 | Igawa et al. |
| 2010/0028372 A1 | 2/2010 | Jezek |
| 2010/0247523 A1 | 9/2010 | Kano et al. |
| 2010/0292443 A1 | 11/2010 | Sabbadini et al. |
| 2010/0297697 A1 | 11/2010 | Ambrosius et al. |
| 2010/0298542 A1 | 11/2010 | Igawa et al. |
| 2011/0076275 A1 | 3/2011 | Igawa et al. |
| 2011/0098450 A1 | 4/2011 | Igawa et al. |
| 2011/0245473 A1 | 10/2011 | Igawa et al. |
| 2012/0253016 A1 | 10/2012 | Igawa et al. |
| 2012/0301460 A1 | 11/2012 | Bao et al. |
| 2013/0022625 A1* | 1/2013 | Igawa ........... A61K 47/183 |
| | | 530/390.5 |
| 2013/0317203 A1 | 11/2013 | Igawa et al. |
| 2013/0330345 A1 | 12/2013 | Igawa et al. |
| 2014/0105889 A1 | 4/2014 | Igawa et al. |
| 2014/0363428 A1 | 12/2014 | Igawa et al. |
| 2015/0050269 A1 | 2/2015 | Igawa et al. |
| 2015/0166666 A1 | 6/2015 | Igawa et al. |
| 2015/0315278 A1 | 11/2015 | Igawa et al. |
| 2016/0139117 A1 | 5/2016 | Yamamura et al. |
| 2016/0159915 A1 | 6/2016 | Igawa et al. |
| 2017/0121412 A1 | 5/2017 | Igawa et al. |
| 2018/0148509 A1 | 5/2018 | Kakehi et al. |
| 2018/0344630 A1 | 12/2018 | Igawa et al. |
| 2019/0085085 A1 | 3/2019 | Igawa et al. |
| 2020/0223940 A1 | 7/2020 | Teranishi et al. |
| 2020/0231688 A1 | 7/2020 | Igawa et al. |
| 2021/0017286 A1 | 1/2021 | Kakehi et al. |
| 2021/0189006 A1 | 6/2021 | Saeki et al. |
| 2021/0206862 A1 | 7/2021 | Igawa et al. |
| 2022/0041741 A1 | 2/2022 | Igawa et al. |
| 2022/0306755 A1 | 9/2022 | Igawa et al. |
| 2024/0010738 A1 | 1/2024 | Igawa et al. |
| 2024/0150477 A1 | 5/2024 | Kakehi et al. |
| 2024/0158518 A1 | 5/2024 | Ozawa et al. |
| 2024/0301075 A1 | 9/2024 | Igawa et al. |
| 2024/0417480 A1 | 12/2024 | Kakehi et al. |

FOREIGN PATENT DOCUMENTS

| | | |
|---|---|---|
| CA | 1 332 367 | 10/1994 |
| CA | 2 203 182 | 5/1996 |
| CA | 2 443 294 | 10/2002 |
| CA | 2 523 577 | 11/2004 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 648 644 | 10/2007 |
| CA | 2 700 394 | 4/2009 |
| CA | 2 700 498 | 4/2009 |
| CN | 1798575 | 7/2006 |
| CN | 1879875 | 12/2006 |
| CN | 101120087 | 2/2008 |
| CN | 101166763 | 4/2008 |
| CN | 101426527 | 5/2009 |
| CN | 101460622 | 6/2009 |
| EP | 0 361 902 A | 4/1990 |
| EP | 0 420 649 A | 4/1991 |
| EP | 0 628 639 A | 12/1994 |
| EP | 0 783 893 A | 7/1997 |
| EP | 1 197 221 A | 4/2002 |
| EP | 1 598 074 A | 11/2005 |
| EP | 1 674 111 A | 6/2006 |
| EP | 1 688 488 A | 8/2006 |
| EP | 1 690 550 A | 8/2006 |
| EP | 1 712 237 A | 10/2006 |
| EP | 1 712 240 A | 10/2006 |
| EP | 1 728 801 A | 12/2006 |
| EP | 1 733 740 A | 12/2006 |
| EP | 1 977 763 A | 10/2008 |
| EP | 2 009 101 A | 12/2008 |
| EP | 2 194 066 A | 6/2010 |
| EP | 2 202 245 A | 6/2010 |
| EP | 2 206 775 A | 7/2010 |
| EP | 2 275 443 A | 1/2011 |
| EP | 2 409 991 A | 1/2012 |
| EP | 1 802 344 B | 8/2012 |
| EP | 2 526 963 A | 11/2012 |
| JP | S55-102519 | 8/1980 |
| JP | H02-163096 | 6/1990 |
| JP | 2002-505086 | 2/2002 |
| JP | 2006-502116 | 1/2006 |
| JP | 2006-512087 | 4/2006 |
| JP | 2007-524602 | 8/2007 |
| JP | 2007-525171 | 9/2007 |
| JP | 2008-536917 | 9/2008 |
| JP | 2009-525986 | 7/2009 |
| JP | 2009-539986 | 11/2009 |
| JP | 5144499 | 2/2013 |
| JP | 5717624 | 5/2015 |
| KR | 2006/0010765 | 2/2006 |
| KR | 2007/0035482 | 3/2007 |
| KR | 2007/0068385 | 6/2007 |
| KR | 2008/0098504 | 11/2008 |
| RU | 2191003 | 10/2002 |
| RU | 2195960 | 1/2003 |
| RU | 2318829 | 3/2008 |
| TW | 2011/38828 | 11/2011 |
| WO | WO 92/19759 | 11/1992 |
| WO | WO 95/09873 | 4/1995 |
| WO | WO 96/11020 | 4/1996 |
| WO | WO 96/12503 | 5/1996 |
| WO | WO 97/04801 | 2/1997 |
| WO | WO 99/43713 | 9/1999 |
| WO | WO 99/58572 | 11/1999 |
| WO | WO 03/039485 | 5/2003 |
| WO | WO 03/068259 | 8/2003 |
| WO | WO 03/068260 | 8/2003 |
| WO | WO 2004/007520 | 1/2004 |
| WO | WO 2004/035752 | 4/2004 |
| WO | WO 2004/039826 | 5/2004 |
| WO | WO 2004/055164 | 7/2004 |
| WO | WO 2004/075913 | 9/2004 |
| WO | WO 2004/091658 | 10/2004 |
| WO | WO 2004/092219 | 10/2004 |
| WO | WO 2004/096273 | 11/2004 |
| WO | WO 2005/005604 | 1/2005 |
| WO | WO 2005/056606 | 6/2005 |
| WO | WO 2005/063291 | 7/2005 |
| WO | WO 2005/080429 | 9/2005 |
| WO | WO 2005/090405 | 9/2005 |
| WO | WO 2006/006693 | 1/2006 |
| WO | WO 2006/023144 | 3/2006 |
| WO | WO 2006/044908 | 4/2006 |
| WO | WO 2006/065746 | 6/2006 |
| WO | WO 2006/069036 | 6/2006 |
| WO | WO 2006/070286 | 7/2006 |
| WO | WO 2006/112838 | 10/2006 |
| WO | WO 2006/119115 | 11/2006 |
| WO | WO 2007/074880 | 7/2007 |
| WO | WO 2007/092772 | 8/2007 |
| WO | WO 2007/109221 | 9/2007 |
| WO | WO 2007/114319 | 10/2007 |
| WO | WO 2007/137984 | 12/2007 |
| WO | WO 2007/143168 | 12/2007 |
| WO | WO 2007/146268 | 12/2007 |
| WO | WO 2008/045373 | 4/2008 |
| WO | WO 2008/071394 | 6/2008 |
| WO | WO 2008/079290 | 7/2008 |

(56) References Cited

FOREIGN PATENT DOCUMENTS

| WO | WO 2008/084237 | 7/2008 |
| WO | WO 2008/086395 | 7/2008 |
| WO | WO 2008/116103 | 9/2008 |
| WO | WO 2008/121615 | 10/2008 |
| WO | WO 2008/132439 | 11/2008 |
| WO | WO 2009/006301 | 1/2009 |
| WO | WO 2009/006338 | 1/2009 |
| WO | WO 2009/041613 | 4/2009 |
| WO | WO 2009/041621 | 4/2009 |
| WO | WO 2009/041643 | 4/2009 |
| WO | WO 2009/072604 | 6/2009 |
| WO | WO 2009/086400 | 7/2009 |
| WO | WO 2009/125825 | 10/2009 |
| WO | WO 2009/141239 | 11/2009 |
| WO | WO 2010/035769 | 4/2010 |
| WO | WO 2010/106812 | 9/2010 |
| WO | WO 2010/107108 | 9/2010 |
| WO | WO 2010/107109 | 9/2010 |
| WO | WO 2010/107110 | 9/2010 |
| WO | WO 2011/090088 | 7/2011 |
| WO | WO 2011/090088 A1 | 7/2011 |
| WO | WO 2012/073992 | 6/2012 |
| WO | WO 2014/200018 | 12/2014 |
| WO | WO 2016/136933 | 9/2016 |
| WO | WO 2016/136933 A1 | 9/2016 |
| WO | WO 2021/241720 | 12/2021 |
| WO | WO 2022/191306 | 9/2022 |
| WO | WO 2023/095852 A1 | 6/2023 |
| WO | WO 2023/140269 A1 | 7/2023 |

OTHER PUBLICATIONS

U.S. Appl. No. 16/983,115, filed Aug. 3, 2020, Kakehi et al.
U.S. Appl. No. 17/097,298, filed Nov. 13, 2020, Igawa et al.
U.S. Appl. No. 17/509,128, filed Oct. 25, 2021, Igawa et al.
U.S. Appl. No. 17/829,641, filed Jun. 1, 2022, Igawa et al.
U.S. Appl. No. 18/096,066, filed Jan. 12, 2023, Igawa et al.
Armour et al., "Recombinant human IgG molecules lacking Fcγ receptor I binding and monocyte triggering activities," Eur J Immunol, Aug. 1999, 29(8):2613-2624.
Bartelds et al., "Clinical response to adalimumab: relationship to anti-adalimumab antibodies and serum adalimumab concentrations in rheumatoid arthritis," Ann Rheum Dis, Feb. 2007, 66(7):921-926.
Bender et al., "Immunogenicity, efficacy and adverse events of adalimumab in RA patients," Rheumatol Int, Jan. 2007, 27(3):269-274.
Bian et al., "Discovery of promiscuous HLA-II-restricted T cell epitopes with TEPITOPE," Methods, Dec. 2004, 34(4):468-475.
Chau et al., "HuM291(Nuvion), a humanized Fc receptor-nonbinding antibody against CD3, anergizes peripheral blood T cells as partial agonist of the T cell receptor," Transplantation., Apr. 2001, 71(7):941-950.
Chien et al., "Significant structural and functional change of an antigen-binding site by a distant amino acid substitution: proposal of a structural mechanism," Proc Natl Acad Sci USA, Jul. 1989, 86(14):5532-5536.
Chirino et al., "Minimizing the immunogenicity of protein therapeutics," Drug Discov Today, Jan. 2004, 9:82-90.
Chu et al., "Accumulation of succinimide in a recombinant monoclonal antibody in mildly acidic buffers under elevated temperatures," Pharm Res, Jun. 2007, 24(6):1145-1156.
Chugai NMO Clinical Trial Webinar, Sakura Star Study, dated Dec. 12, 2014, downloaded on Sep. 5, 2019 from https://3.amazonaws.com/gicf-wp-uploads/wp-content/uploads/2016/05/16162202/12_12_14_Chugai_Webinar_PPT_Complete_Deck_FINAL.pdf, 18 pages.
ClinicalTrials.gov, "A Phase 2a Study to Evaluate the Effects of Sirukumab in Subjects With Severe Poorly Controlled Asthma," Id: NCT02794519, Sponsored by GlaxoSmithKline, Jun. 9, 2016 (https://clinicaltrials.gov/ct2/show/NCT02794519).
Cole et al., "Human IgG2 variants of chimeric anti-CD3 are nonmitogenic to T cells," J Immunol, Oct. 1997, 159(7):3613-3621.

Cordoba et al., "Non-enzymatic hinge region fragmentation of antibodies in solution," J Chromatogr B Analyt Technol Biomed Life Sci, Apr. 2005, 818(2):115-121.
Cuatrecasas et al., "Affinity Chromatography," Methods Enzymol, 1971, 12:345-378.
Dall'Acqua et al., "Properties of Human IgG1s Engineered for Enhanced Binding to the Neonatal Fc Receptor (FcRn)," J Biol Chem, Aug. 18, 2006, 281(33):23514-23524. Epub Jun. 21, 2006.
Damschroder et al., "Framework shuffling of antibodies to reduce immunogenicity and manipulate functional and biophysical properties," Mol Immunol, Apr. 2007, 44(11):3049-3060.
Davies et al., "Affinity improvement of single antibody VH domains: residues in all three hypervariable regions affect antigen binding," Sep. 1996, Immunotechnology, 2(3): 169-179.
De Pascalis et al., "Grafting of 'abbreviated' complementarity-determining regions containing specificity-determining residues essential for ligand contact to engineer a less immunogenic humanized monoclonal antibody," J Immunol, Sep. 2002, 169(6):3076-3084.
Dhiman et al., "Gene expression microarrays: a 21st century tool for directed vaccine design," Vaccine, Oct. 12, 2001;20(1-2):22-30.
Durkee et al., "Immunoaffinity chromatographic purification of Russell's viper venom factor X activator using elution in high concentrations of magnesium chloride," Protein Expr Purif, Oct. 1993, 4(5):405-411.
Ewert et al., "Stability improvement of antibodies for extracellular and intracellular applications: CDR grafting to stable frameworks and structure-based framework engineering," Methods, Oct. 2004, 34:184-199.
F. Hoffmann-La Roche Ltd., "Efficacy and Safety Study of Satralizumab (SA237) as Add-on Therapy to Treat Participants With Neuromyelitis Optica (NMO) and NMO Spectrum Disorder (NMOSD)," Study NCT02028884, first posted on clinicaltrialsregister.eu on Jan. 7, 2014 and last updated on Feb. 17, 2022; downloaded from clinicaltrialsregister.eu archive on Jan. 11, 2023, https://clinicaltrials.gov/ct2/show/NCT02028884.
F. Hoffmann-La Roche Ltd., "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, first posted on clinicaltrialsregister.eu on Feb. 27, 2014 and last updated on Feb. 25, 2022; downloaded from clinicaltrialsregister.eu archive on Jan. 11, 2023, https://clinicaltrials.gov/ct2/show/study/NCT02073279?show_locs=Y#locn.
F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Germany; submitted to clinicaltrialsregister.eu on Dec. 20, 2013; downloaded from clinicaltrialsregister.eu archive on Sep. 23, 2021, https://www.clinicaltrialsregister.eu/ctr-search/trial/2013-003752-21/DE, 7 pages.
F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in the United Kingdom; submitted to clinicaltrialsregister.eu on Oct. 15, 2013; downloaded from clinicaltrialsregister.eu archive on Sep. 23, 2021, https://www.clinicaltrialsregister.eu/ctr-search/trial/2013-003752-21/GB, 6 pages.
F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Italy; submitted to clinicaltrialsregister.eu on Feb. 6, 2014; downloaded from clinicaltrialsregister.eu archive on Sep. 23, 2021, https://www.clinicaltrialsregister.eu/ctr-search/trial/2013-003752-21/IT. 5 pages.
F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Poland;

(56) References Cited

OTHER PUBLICATIONS submitted to clinicaltrialsregister.eu on Jul. 4, 2014; downloaded from clinicaltrialsregister.eu archive on Sep. 23, 2021, https://www.clinicaltrialsregister.eu/ctr-search/trial/2013-003752-21/PL, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltrialsregister.eu/ctr-search/trial/2013-003752-21/HU, 6 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Spain; submitted to clinicaltrialsregister.eu on Mar. 11, 2015; downloaded from clinicaltrialsregister.eu archive on Sep. 23, 2021, https://www.clinicaltrialsregister.eu/ctr-search/trial/2013-003752-21/ES. 7 pages.

F. Hoffmann-La Roche Ltd., "A Multicenter, Randomized, Double-blind, Placebo-controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41 in Croatia; submitted to clinicaltrialsregister.eu on Dec. 15, 2016; downloaded from clinicaltrialsregister.eu archive on Dec. 3, 2021, https://www.clinicaltrialsregister.eu/ctr-search/trial/2015-005431-41/HR, 6 pages.

Gessner et al., "The IgG Fc receptor family," Ann Hematol, Jun. 1998, 76(6):231-248.

Ghetie et al., "Increasing the serum persistence of an IgG fragment by random mutagenesis," Nat Biotechnol, Jul. 1997, 15:637-640.

Guyre et al., "Increased potency of Fc-receptor-targeted antigens," Cancer Immunol Immunother, Nov. 1997/Dec. 45(3-4):146-148.

Hanes et al., "Picomolar affinity antibodies from a fully synthetic naive library selected and evolved by ribosome display," Nat Biotechnol, Dec. 2000, 18(12): 1287-1292.

Hinton et al., "An engineered human IgG1 antibody with longer serum half-life," J Immunol, Jan. 2006, 176:346-356.

Holt et al., "Domain antibodies: proteins for therapy," Trends Biotechnol, Nov. 2003, 21(11):484-490.

Huizinga et al., "Sarilumab, a fully human monoclonal antibody against IL-6Rα in patients with rheumatoid arthritis and an inadequate response to methotrexate: efficacy and safety results from the randomised SARIL-RA-MOBILITY Part A trial," Ann Rheum Dis, Sep. 2014, 73(9):1626-1634. doi: 10. 1136/annrheumdis-2013-204405. Epub Dec. 2, 2013.

Hwang et al., "Use of human germline genes in a CDR homology-based approach to antibody humanization," Methods, May 2005, 36:35-42.

Johnson et al., "Cation exchange-HPLC and mass spectrometry reveal C-terminal amidation of an IgG1 heavy chain," Anal Biochem, Jan. 2007, 360:75-83.

Jones et al., "Identification and removal of a promiscuous CD4+ T cell epitope from the C1 domain of factor VIII," Thromb Haemost, May 2005, 3:991-1000.

Kim et al., "Antibody engineering for the development of therapeutic antibodies," Mol Cells, Aug. 2005, 20:17-29.

Maini et al., "Double-blind randomized controlled clinical trial of the interleukin-6 receptor antagonist, tocilizumab, in European patients with rheumatoid arthritis who had an incomplete response to methotrexate," Arthritis Rheum, Aug. 2006, 54:2817-28129.

Maynard et al., "Antibody engineering," Annu Rev Biomed Eng, 2000, 2:339-376.

Mihara et al., "Tocilizumab inhibits signal transduction mediated by both mIL-6R and sIL-6R, but not by the receptors of other members of IL-6 cytokine family," Int Immunopharmacol, Nov. 2005, 5(12):1731-1740.

Nishimoto et al., "Humanized anti-interleukin-6 receptor antibody treatment of multicentric Castleman disease," Blood, Oct. 2005, 106:2627-2632.

Nishimoto et al., "Interleukin 6: from bench to bedside," Nat Clin Pract Rheumatol, Nov. 2006, 2(11):619-626.

Ohno et al., "Antigen-binding specificities of antibodies are primarily determined by seven residues of $V_H$," Proc Natl Acad Sci USA, May 1985, 82(9):2945-2949.

Ohsugi et al., "Current Antibody Drugs ~ Developments/ Manufacturing Technology/Scope of Patents," Pharm Stage, 2007, 7(5):13-18 (with English translation).

Okiyama et al., "Therapeutic Effects of Interleukin-6 Blockade in a Murine Model of Polymyositis That Does Not Require Interleukin-17A," Arthritis & Rheumatism, Aug. 2009, 60(8):2505-2512.

Padlan et al., "Structure of an antibody-antigen complex: crystal structure of the HyHEL-10 Fab-lysozyme complex," Proc Natl Acad Sci USA, Aug. 1989, 86:5938-5942.

Pavlou et al., "The therapeutic antibodies market to 2008," Eur J Pharm Biopharm, Apr. 2005, 59:389-396.

Pini et al., "Design and use of a phage display library. Human antibodies with subnanomolar affinity against a marker of angiogenesis eluted from a two-dimensional gel," J Biol Chem, Aug. 1998, 273(34):21769-21776.

Rajpal et al., "A general method for greatly improving the affinity of antibodies by using combinatorial libraries," Proc Natl Acad Sci USA, Jun. 2005, 102:8466-8471.

Reddy et al., "Elimination of Fc receptor-dependent effector functions of a modified IgG4 monoclonal antibody to human CD4," J Immunol, Feb. 2000, 164(4): 1925-1933.

Reichert et al., "Monoclonal antibody successes in the clinic," Nat Biotechnol, Sep. 2005, 23:1073-1078.

Rothe et al., "Ribosome display for improved biotherapeutic molecules," Expert Opin Biol Ther, Feb. 2006, 6:177-187.

Rudikoff et al., "Single amino acid substitution altering antigen-binding specificity," Proc Natl Acad Sci USA, Mar. 1982, 79(6):1979-1983.

Salfeld et al., "Isotype selection in antibody engineering," Nat Biotechnol, Dec. 2007, 25:1369-1372.

Sato et al., "Reshaping a human antibody to inhibit the interleukin 6-dependent tumor cell growth," Cancer Res, Feb. 1993, 53:851-856.

Sebba et al., "Tocilizumab: the first interleukin-6-receptor inhibitor," Am J Health Syst Pharm, Aug. 1, 2008, 65(15):1413-1418. doi: 10.2146/ajhp070449.

Shire et al., "Challenges in the development of high protein concentration formulations," J Pharm Sci, Jun. 2004, 93:1390-1402.

Strand et al., "Biologic therapies in rheumatology: lessons learned, future directions," Nat Rev Drug Discov, Jan. 2007, 6:75-92.

Takkinen et al., "Affinity and Specificity Maturation by CDR Walking," Antibody Engineering, Springer Lab Manuals, 2001, pp. 540-545.

Tan et al., "Engineering the isoelectric point of a renal cell carcinoma targeting antibody greatly enhances scFv solubility," Immunotechnology, Oct. 1998, 4(2):107-114.

Teeling et al., "The biological activity of human CD20 monoclonal antibodies is linked to unique epitopes on CD20," J Immunol, Jul. 2006, 177(1):362-371.

Thies et al., "The alternatively folded state of the antibody $C_H3$ domain," J Mol Biol, Jun. 22, 2001, 309(5):1077-1085.

Vajdos et al., "Comprehensive functional maps of the antigen-binding site of an anti-ErbB2 antibody obtained with shotgun scanning mutagenesis," J Mol Biol, Jul. 2002, 320(2):415-428.

Van Walle et al., "Immunogenicity screening in protein drug development," Expert Opin Biol Ther, Mar. 2007, 7(3):405-418.

Wikipedia, "Chaotropic agent," Oct. 7, 2015, Retrieved from the Internet on Nov. 2, 2015: https://en.wikipedia.org/wiki/Chaotropic_agent.

Wu et al., "Development of motavizumab, an ultra-potent antibody for the prevention of respiratory syncytial virus infection in the upper and lower respiratory tract," J Mol Biol, May 2007, 368:652-665.

(56) References Cited

OTHER PUBLICATIONS

Wu et al., "Humanization of a murine monoclonal antibody by simultaneous optimization of framework and CDR residues," J Mol Biol, 2999 Nov, 294(1):151-162.

Yamamura et al., "A double-blind placebo-controlled study of satralizumab (SA237), a recycling anti-IL-6 receptor monoclonal antibody, as add-on therapy for neuromyelitis optica (NMO) and NMO spectrum disorder (NMOSD)," European Journal of Neurology, 2018, 25 (Suppl. 2), p. 536, abstract EPR3103 for presentation given on Jun. 16, 2018. EPR3103 (https://ipp-ean18.netkey.at/index.php?p=recorddetail&rid=f16c1ff3-f5ec-4b71-8a99-7c39bdc90418&t).

International Search Report in PCT/JP2021/020337, mailed Jun. 29, 2021, 2 pages.

U.S. Appl. No. 18/411,372, filed Jan. 12, 2024, Kakehi et al.

Grapentin et al., "Protein-Polydimethylsiloxane Particles in Liquid Vial Monoclonal Antibody Formulations Containing Poloxamer 188," J Pharm Sci, Aug. 2020, 109(8):2393-2404.

U.S. Appl. No. 18/174,043, filed Feb. 24, 2023, Igawa et al.

Agrisera AB, "Molecular weight and isoelectric point of various animal immunoglobulins," 2 pages, printed from the Internet Nov. 1, 2021 at https://www.agrisera.com/en/info/molecular-weight-and-isoelectric-point-of-various-animal-immunoglobulins.

Arakawa et al., "Biotechnology applications of amino acids in protein purification and formulations," Amino Acids, Nov. 2007, 33(4):587-605. Epub Mar. 16, 2007.

"Biotechnology Pharmaceutical Formulation," 2007 National Licensed Pharmacist Continuing Education Textbook, China Licensed Pharmacist Association eds., China Tradition Chinese Medicine Press, 2007, pp. 336-345 (with English translation).

Brown et al., "Tolerance to Single, but Not Multiple, Amino Acid Replacements in Antibody $V_H$ CDR2," J Immunol, May 1, 1996, 156(9):3285-3291.

Chang et al., "Practical Approaches to Protein Formulation Development," Pharm Biotechnol, 2002, 13:1-25.

Chen et al., "Influence of histidine on the stability and physical properties of a fully human antibody in aqueous and solid forms," Pharm Res, Dec. 2003, 20(12):1952-1960. doi: 10.1023/b:pham.0000008042.15988.c0.

Daugherty et al., "Formulation and delivery issues for monoclonal antibody therapeutics," Adv Drug Deliv Rev, Aug. 7, 2006, 58(5-6):686-706. Epub May 22, 2006.

Dillon et al., "Structural and Functional Characterization of Disulfide Isoforms of the Human IgG2 Subclass," J Biol Chem, Jun. 6, 2008, 283(23):16206-16215. Epub Mar. 12, 2008.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 23, 2021 as https://www.clinicaltrialsregister.eu/ctr-search/trial/2013-003752-21/HU, 6 pages.

"Formulation of Protein- and Peptide-Based Parenteral Products," Pharmaceutical Dosage Forms, Parenteral Medications 3rd ed., NEMA et al. eds, 2010, p. 237, Table 2.

Frokjaer et al., "Protein Drug Stability: A Formulation Challenge," Nat Rev Drug Discov, Apr. 2005, 4(4):298-306.

Gokarn et al., "Self-Buffering Antibody Formulations," J Pharm Sci, Aug. 2008, 97(8):3051-3066.

Golovanov et al., "A simple method for improving protein solubility and long-term stability," J Am Chem Soc, Jul. 28, 2004, 126(29):8933-8939.

Hager's Handbook of the Pharmaceutical Practice, 5th ed., Nuernberg et al. eds., 1991, pp. 758-761 (with English translation).

Hautbergue et al., "Increasing the sensitivity of cryoprobe protein NMR experiments by using the sole low-conductivity arginine glutamate salt," J Magn Reson, Apr. 2008, 191(2):335-339. doi: 10.1016/j.jmr.2007.12.017. Epub Jan. 3, 2008.

Ishihara et al., "Accelerated purification process development of monoclonal antibodies for shortening time to clinic—Design and case study of chromatography processes," J Chromatogr A, Dec. 28, 2007, 1176(1-2):149-156. Epub Nov. 7, 2007.

Ito et al., "The His-probe method: effects of histidine residues introduced into the complementarity-determining regions of antibodies on antigen-antibody interactions at different pH values," FEBS Lett, Aug. 31, 1992, 309(1):85-88.

Kheddo et al., "The effect of arginine glutamate on the stability of monoclonal antibodies in solution," Int J Pharm, Oct. 1, 2014, 473(1-2):126-133. doi: 10.1016/j.ijpharm.2014.06.053. Epub Jun. 30, 2014.

"Liquid Formulation Strategies," Formulation and Process Development Strategies for Manufacturing Biopharmaceuticals, Jameel et al. eds, Jul. 13, 2010, p. 403.

Liu et al., "Prediction of the isoelectric point of an amino acid based on GA-PLS and SVMs," J Chem Inf Comput Sci, Jan.-Feb. 2004, 44(1):161-167. doi: 10.1021/ci034173u.

MacCallum et al., "Antibody-antigen Interactions: Contact Analysis and Binding Site Topography," J Mol Biol, Oct. 11, 1996, 262(5):732-745.

Mahler et al., "Protein aggregation: pathways, induction factors and analysis," J Pharm Sci, Sep. 2009, 98(9):2909-2934. doi: 10.1002/jps.21566.

Manz et al., "Bioanalytical Chemistry," Bioanalytical Chemistry, 2004, pp. 2-7.

Nishimoto, "Humanized anti-IL-6 Receptor Antibody (Tocilizumab)," Nihon Rinsho, Jul. 2007, 65(7):1218-1225 (with English translation).

Nishimoto et al., "Humanized Antihuman IL-6 Receptor Antibody, Tocilizumab," Handb Exp Pharmacol, 2008, 181:151-160.

Nishimoto et al., "Anti-interleukin 6 receptor antibody treatment in rheumatic disease," Ann Rheum Dis, Nov. 2000, 59 Suppl 1:i21-i27.

"Non-specific staining and staining control," Modern Cytochemistry Technology and Its Application in Chinese and Western Medicine, XIE ed., 1998, pp. 154-158 (with English translation).

Onda et al., "Lowering the Isoelectric Point of the Fv Portion of Recombinant Immunotoxins Leads to Decreased Nonspecific Animal Toxicity without Affecting Antitumor Activity," Cancer Res, Jul. 1, 2001, 61(13):5070-5077.

Philippovich, Fundamentals of Biochemistry, Moscow, 1969, p. 31 (with English translation).

Pokrovsky, Soviet Encyclopedia, Moscow, 1991, p. 146 (with English translation).

"Powder Bases," ROMPP Encyclopedia, Chemistry, 10th ed., Falbe et al. eds, 1988, pp. 3618-3619 (with English translation).

Shire, "Formulation and manufacturability of biologics," Curr Opin Biotechnol, Dec. 2009, 20(6):708-714. Epub Oct. 31, 2009.

Summary of Product Characteristics for the Product Xolair by Novartis Europharm Limited, European Medicines Agency (https://www.ema.europa.eu), first authorization: Oct. 25, 2005; latest renewal: Jun. 22, 2015, 68 pages.

Valente et al., "Second virial coefficient studies of cosolvent-induced protein self-interaction," Biophys J, Dec. 2005, 89(6):4211-4218. doi: 10.1529/biophysj.105.068551. Epub Sep. 30, 2005.

Wang et al., "Minireview—Antibody Structure, Instability, and Formulation," J Pharm Sci, Jan. 2007, 96(1):1-26.

Xolair Regulatory Documents, European Medicines Agency—Science Medicines Health, Jul. 28, 2010, 11 pages.

Zumdahl, Chapter 8 "Applications of Aqueous Equilibria," Chemical Principals (Instructor's Copy), 6th ed., 2009, pp. 300-312.

U.S. Appl. No. 18/330,420, filed Jun. 7, 2023, Kakehi et al.

Desai et al., "An Intercompany Perspective on Practical Experiences of Predicting, Optimizing and Analyzing High Concentration Biologic Therapeutic Formulations," J Pharm Sci, Feb. 2023, 112(2):359-369.

Huang et al., "Penpulimab, an Fc-Engineered IgG1 Anti-PD-1 Antibody, With Improved Efficacy and Low Incidence of Immune-Related Adverse Events," Front Immunol, Jun. 27, 2022, 13:924542, 12 pages.

Schermeyer et al., "Characterization of highly concentrated antibody solution—A toolbox for the description of protein long-term solution stability," mAbs, Oct. 2017, 9(7):1169-1185.

(56) References Cited

OTHER PUBLICATIONS

U.S. Appl. No. 18/712,917, filed May 23, 2024, Ozawa et al.
Katagiri et al., "Effects of SA237, a Humanized Anti-Interleukin-6
Receptor Monoclonal Antibody, on Pre- and Postnatal Development
in Cynomolgus Monkey," Birth Defects Res, Jul. 3, 2017, 109(11):843-856.
U.S. Appl. No. 18/633,674, filed Apr. 12, 2024, Igawa et al.
U.S. Appl. No. 18/651,896, filed May 1, 2024, Igawa et al.
U.S. Appl. No. 18/280,970, filed Sep. 8, 2023, Ozawa et al.
U.S. Appl. No. 18/464,407, filed Sep. 11, 2023, Igawa et al.
U.S. Appl. No. 18/956,095, filed Nov. 22, 2024, Igawa et al.
U.S. Appl. No. 18/975,370, filed Dec. 10, 2024, Igawa et al.
USPTO Restriction Requirement in U.S. Appl. No. 13/522,848,
dated Oct. 23, 2014, 5 pages.
USPTO Non-Final Office Action in U.S. Appl. No. 13/522,848,
dated May 1, 2015, 8 pages.
USPTO Final Office Action in U.S. Appl. No. 13/522,848, dated
Jan. 4, 2016, 7 pages.
USPTO Non-Final Office Action in U.S. Appl. No. 13/522,848,
dated Sep. 20, 2016, 7 pages.
USPTO Final Office Action in U.S. Appl. No. 13/522,848, dated
May 11, 2017, 7 pages.

* cited by examiner

ANTIBODY-CONTAINING FORMULATION

CROSS-REFERENCE TO RELATED APPLICATIONS

This application is the National Stage of International Application No. PCT/JP2021/020337, filed on May 28, 2021, which claims the benefit of Japanese Application No. 2020-094716, filed on May 29, 2020.

SEQUENCE LISTING

This application contains a Sequence Listing that has been submitted electronically as an ASCII text file named SequenceListing.txt. The ASCII text file, created on Sep. 20, 2022, is 9,622 bytes in size. The material in the ASCII text file is hereby incorporated by reference in its entirety.

TECHNICAL FIELD

The present invention relates to stable formulations comprising an antibody containing a heavy chain variable region which contains a CDR1 having the sequence of SEQ ID NO: 1, a CDR2 having the sequence of SEQ ID NO: 2, and a CDR3 having the sequence of SEQ ID NO: 3, and a light chain variable region which contains a CDR1 having the sequence of SEQ ID NO: 4, CDR2 having the sequence of SEQ ID NO: 5, and a CDR3 having the sequence of SEQ ID NO: 6. The present invention also relates to a method of stabilizing a solution comprising an anti-IL-6 receptor antibody, a method of suppressing the association (for example, dimerization) of the antibody, and a method of suppressing the generation of insoluble particles in a solution comprising the antibody.

SA237 (satralizumab) is a modified IgG2 humanized anti-human IL-6 receptor neutralizing antibody designed to extend the half-life in plasma by modifying the amino acid sequence of tocilizumab, which is an IgG1 antibody. Compared to tocilizumab, SA237 has features such as 1) prolonged plasma half-life by pH-dependent IL-6 receptor binding, lowered antibody isoelectric point, and enhanced binding to FcRn under acidic conditions; and 2) reduced effector action such as ADCC/CDC by reduced Fc7 receptor binding ability and adoption of an IgG2 structure.

Clinical trials of SA237 have been conducted in patients with neuromyelitis optica spectrum disorder (NPLs 1 to 7), and the SA237 is now at the stage of application for the manufacture and sales approval in Japan, the United States, and Europe.

Various antibody formulations have been developed in recent years and are actually in use. Many of these formulations are used for intravenous injection. Meanwhile, formulations for subcutaneous administration are considered to be desirable in the case of chronic autoimmune diseases. Since the amount of antibody per single dose in subcutaneous administrations is large (about 100 mg to 200 mg) and the volume for subcutaneous injection is generally limited, it is necessary to increase the antibody concentration in the solution when designing an antibody-containing formulation for subcutaneous administration.

Undesirable degradation including the formation of insoluble and/or soluble aggregates occurs in solutions containing high concentration of antibody. These insoluble aggregates and soluble aggregates are likely to be formed in the liquid state due to the association of antibody molecules. When a liquid formulation is stored for a long period of time, deamidation of asparagine residues may result in loss or reduction of the bioactivity of the antibody molecules. Freeze and thaw cycles also cause the formation of degraded antibody molecules and aggregated antibody molecules.

Various concepts have been proposed in order to provide stabilized formulations in which the reduction of the active ingredient is suppressed even after long-term storage of the formulations. Such formulations are obtained by dissolving the active ingredient and various additives in a buffer solution. There is a need to provide high-concentration antibody-containing formulations that are stable and suitable for use in subcutaneous administrations where dimer formation and deamidation during long-term storage are inhibited. So far, as a general-purpose technology related to stabilization of antibody-containing formulations, a stabilizing effect has been reported by using aspartic acid or glutamic acid, which are acidic amino acids as a counterion species of histidine buffer and as a counterion species of basic amino acids such as arginine used as a stabilizer (Non-Patent Literature (NPL)-1). Moreover, as effects of surfactants added to formulations, it has been reported that Poloxamer 188 has a superior effect of suppressing oxidation of protein solution formulations than polysorbates (NPL-2). Meanwhile, regarding formulations containing SA237, examples using histidine-HCl or citric acid as a buffer and arginine or a sugar (trehalose or the like) as a stabilizer have been reported (NPL-3). However, there is a need for developing more stable SA237-comprising formulations in which the formation of aggregates and/or the generation of insoluble particles are suppressed for a long period of time under storage conditions.

CITATION LIST

Non-Patent Literature

[NPL 1] https://clinicaltrials.gov/ct2/show/NCT02028884
[NPL 2] https://clinicaltrials.gov/ct2/show/study/NCT02073279?show_locs=Y #locn
[NPL 3] https://www.clinicaltrialsregister.eu/ctr-search/search?query=SA-307JG
[NPL 4] https://www.clinicaltrialsregister.eu/ctr-search/trial/2015-005431-41/HR
[NPL 5] https://s3.amazonaws.com/gjcf-wp-uploads/wp-content/uploads/2016/05/16162202/12_12_14_Chugai_Webinar_PPT_Complete_Deck_FINAL.pdf
[NPL 6] EAN the home of neurology EPR3103 (https://ipp-ean18.netkey.at/index.php?p=recorddetail&rid=fl6c1ff3-f5ec-4b71-8a99-7c39bdc90418&t)

Patent Literature

[PTL 1] WO2011/090088
[PTL 2] WO2004/075913
[PTL 3] WO2010/106812

SUMMARY OF THE INVENTION

Technical Problem

In one non-limiting embodiment, an objective of the present disclosure is to provide a long-term stable formulation comprising an anti-IL-6 receptor antibody (satralizumab: SA237) as an active ingredient.

Solution to Problem

As a result of diligent research to achieve the above objective, the present inventors discovered that a good effect of suppressing aggregate generation can be obtained when using arginine as an isotonic agent in a formulation comprising an anti-IL-6 receptor antibody (satralizumab: SA237), rather than when using a sugar. It was also found that a good effect of suppressing aggregate generation can be obtained when using aspartic acid or glutamic acid as a counterion species of a histidine buffer solution than when using a chloride ion. Furthermore, it was found that addition of Poloxamer 188 at a predetermined concentration to the formulation suppresses the generation of insoluble particles in the formulation.

The present disclosure is based on such findings and specifically encompasses the embodiments exemplified below.

[1] An antibody solution formulation comprising:
    50 to 250 mg/mL of an antibody comprising
        a heavy chain variable region which comprises a CDR1 having the sequence of SEQ ID NO: 1, a CDR2 having the sequence of SEQ ID NO: 2, and a CDR3 having the sequence of SEQ ID NO: 3, and
        a light chain variable region which comprises a CDR1 having the sequence of SEQ ID NO: 4, a CDR2 having the sequence of SEQ ID NO: 5, and a CDR3 having the sequence of SEQ ID NO: 6;
    10 to 100 mM histidine-aspartate buffer or histidine-glutamate buffer;
    0.1 mg/mL to 2.0 mg/mL of Poloxamer 188; and
    5 mM to 300 mM of arginine,
wherein the pH of the formulation is 5.5 to 6.6.

[2] The formulation according to [1], which is a solution formulation that is not a reconstituted solution of a lyophilized formulation.

[3] A lyophilized formulation which is a composition resulting from lyophilizing a solution comprising:
    50 to 250 mg/mL of an antibody comprising
        a heavy chain variable region which comprises a CDR1 having the sequence of SEQ ID NO: 1, a CDR2 having the sequence of SEQ ID NO: 2, and a CDR3 having the sequence of SEQ ID NO: 3, and
        a light chain variable region which comprises a CDR1 having the sequence of SEQ ID NO: 4, a CDR2 having the sequence of SEQ ID NO: 5, and a CDR3 having the sequence of SEQ ID NO: 6;
    10 to 100 mM histidine-aspartate buffer or histidine-glutamate buffer;
    0.1 mg/mL to 2.0 mg/mL of Poloxamer 188; and
    5 mM to 300 mM of arginine,
wherein the pH of the formulation after reconstitution in water is 5.5 to 6.6.

[4] The formulation according to any one of [1] to [3], which is substantially free of sugars.

[5] The formulation according to any one of [1] to [4], wherein antibody association is suppressed.

[6] The formulation according to any one of [1] to [5], wherein the dimerization of the antibody is reduced.

[7] The formulation according to any one of [1] to [6], wherein the dimerization of the antibody is inhibited.

[8] The formulation according to any one of [1] to [7], wherein the generation of foreign matter is suppressed.

[9] The formulation according to any one of [1] to [8], wherein the generation of insoluble particles is suppressed.

[10] The formulation according to any one of [1] to [9], wherein the generation of insoluble visible particles is suppressed.

[11] A formulation for injection, comprising:
    (i) a container, and
    (ii) an antibody solution formulation which comprises, per 1 mL of solution in the container,
        50 to 250 mg of an antibody comprising
            a heavy chain variable region which comprises a CDR1 having the sequence of SEQ ID NO: 1, a CDR2 having the sequence of SEQ ID NO: 2, and a CDR3 having the sequence of SEQ ID NO: 3, and
            a light chain variable region which comprises a CDR1 having the sequence of SEQ ID NO: 4, a CDR2 having the sequence of SEQ ID NO: 5, and a CDR3 having the sequence of SEQ ID NO: 6;
        0.9 to 52.3 mg of L-arginine;
        1.6 to 15.5 mg of L-histidine;
        0.1 mg to 2.0 mg of Poloxamer 188; and
        L-aspartic acid or L-glutamic acid, and
    which has a pH of 5.5 to 6.6.

[12] A formulation for injection, comprising:
    (i) a container, and
    (ii) an antibody solution formulation which comprises, per 1 mL of solution in the container,
        60 to 200 mg of an antibody comprising
            a heavy chain variable region which comprises a CDR1 having the sequence of SEQ ID NO: 1, a CDR2 having the sequence of SEQ ID NO: 2, and a CDR3 having the sequence of SEQ ID NO: 3, and
            a light chain variable region which comprises a CDR1 having the sequence of SEQ ID NO: 4, a CDR2 having the sequence of SEQ ID NO: 5, and a CDR3 having the sequence of SEQ ID NO: 6;
        8.7 to 26.1 mg of L-arginine;
        1.6 to 6.2 mg of L-histidine;
        0.15 mg to 1.0 mg of Poloxamer 188; and
        L-aspartic acid or L-glutamic acid, and
    which has a pH of 5.5-6.3.

[13] A formulation for injection, comprising:
    (i) a container, and
    (ii) an antibody solution formulation which comprises, per 1 mL of solution in the container,
        120 mg of an antibody comprising
            a heavy chain variable region which comprises a CDR1 having the sequence of SEQ ID NO: 1, a CDR2 having the sequence of SEQ ID NO: 2, and a CDR3 having the sequence of SEQ ID NO: 3, and
            a light chain variable region which comprises a CDR1 having the sequence of SEQ ID NO: 4, a CDR2 having the sequence of SEQ ID NO: 5, and a CDR3 having the sequence of SEQ ID NO: 6;
        26.1 mg of L-arginine;
        3.1 mg of L-histidine;
        0.5 mg of Poloxamer 188; and
        L-aspartic acid or L-glutamic acid, and
    which has a pH of 5.8-6.2.

[14] The formulation according to any one of [1] to [13], wherein the antibody comprises the heavy chain variable region of SEQ ID NO: 8 and the light chain variable region of SEQ ID NO: 7.

[15] The formulation according to any one of [1] to [14], wherein the antibody comprises a heavy chain comprising the sequence of SEQ ID NO: 10 and a light chain comprising the sequence of SEQ ID NO: 9.

[16] The formulation according to any one of [1] to [15], which is for subcutaneous administration.

[17] The formulation according to any one of [1] to [16], which is stable at 2 to 8° C. for at least 6 months.

[18] The formulation according to any one of [1] to [17], wherein the proportion of aggregates at 2 to 8° C. is 2.0% or less, 1.4% or less, or 0.8% or less for at least 6 months, at least 9 months, at least 12 months, at least 15 months, at least 18 months, at least 24 months, or at least 30 months.

[19] A method of stabilizing a solution comprising an antibody, wherein the method comprises the step of adding L-aspartic acid or L-glutamic acid to the solution, wherein the antibody comprises a heavy chain variable region which comprises a CDR1 having the sequence of SEQ ID NO: 1, a CDR2 having the sequence of SEQ ID NO: 2, and a CDR3 having the sequence of SEQ ID NO: 3, and a light chain variable region which comprises a CDR1 having the sequence of SEQ ID NO: 4, a CDR2 having the sequence of SEQ ID NO: 5, and a CDR3 having the sequence of SEQ ID NO: 6.

[20] A method of suppressing antibody association, wherein the method comprises the step of adding L-aspartic acid or L-glutamic acid to a solution comprising the antibody, wherein the antibody comprises a heavy chain variable region which comprises a CDR1 having the sequence of SEQ ID NO: 1, a CDR2 having the sequence of SEQ ID NO: 2, and a CDR3 having the sequence of SEQ ID NO: 3, and a light chain variable region which comprises a CDR1 having the sequence of SEQ ID NO: 4, a CDR2 having the sequence of SEQ ID NO: 5, and a CDR3 having the sequence of SEQ ID NO: 6.

[21] A method of suppressing dimerization of an antibody, wherein the method comprises the step of adding L-aspartic acid or L-glutamic acid to a solution comprising the antibody, wherein the antibody comprises a heavy chain variable region which comprises a CDR1 having the sequence of SEQ ID NO: 1, a CDR2 having the sequence of SEQ ID NO: 2, and a CDR3 having the sequence of SEQ ID NO: 3, and a light chain variable region which comprises a CDR1 having the sequence of SEQ ID NO: 4, a CDR2 having the sequence of SEQ ID NO: 5, and a CDR3 having the sequence of SEQ ID NO: 6.

[22] A method of suppressing the generation of insoluble particles in a solution comprising an antibody, wherein the method comprises the step of adding L-aspartic acid or L-glutamic acid to the solution, wherein the antibody comprises a heavy chain variable region which comprises a CDR1 having the sequence of SEQ ID NO: 1, a CDR2 having the sequence of SEQ ID NO: 2, and a CDR3 having the sequence of SEQ ID NO: 3, and a light chain variable region which comprises a CDR1 having the sequence of SEQ ID NO: 4, a CDR2 having the sequence of SEQ ID NO: 5, and a CDR3 having the sequence of SEQ ID NO: 6.

[23] The method according to [19] or [22], further comprising the step of adding Poloxamer 188 such that its concentration in the solution becomes 0.1 mg/mL to 2.0 mg/mL.

DESCRIPTION OF EMBODIMENTS

Preferred non-limiting embodiments of the present disclosure will be hereinafter described.

All the embodiments set forth in the Examples below are described with the intention that they are naturally construed as being equivalently described in the "Description of Embodiments" of the present specification, without being restricted by any patent practice, conventions, or law that may interpret the contents of the Examples in a limiting manner, in a country where it is intended that the protection of the present patent application be sought.

For descriptions for numerical values in the present disclosure, a numerical value at the smallest digit (for example, ones place) may include values in which one place smaller than the smallest digit (for example, when the smallest digit is ones place, first decimal place) is rounded off. For example, it is intended that the numerical value "5" comprises numerical values comprised in the rages of 4.5 to 5.4.

[Stable Antibody-Containing Formulations Comprising an Anti-IL-6 Receptor Antibody]

To evaluate the storage stability of a sample comprising an anti-IL-6 receptor antibody, the inventors evaluated effects of various additives using a thermal accelerated test (e.g., a severe test at 40° C. or an accelerated test at 25° C.), a storage test under recommended storage conditions (for example, 2 to 8° C., for example, 5° C.), and a freeze-thaw test. As a result, it was found that when using histidine buffer as a buffer to prepare an anti-IL-6 receptor antibody-containing formulation, aggregate generation was suppressed as compared to when using a citrate buffer. It was also found that when the pH of the formulation in solution state was made 5.5, 6.0, or 6.3, the effect of suppressing aggregates was higher than that obtained with a pH of 4.5 or 5.0. Furthermore, it was found that when adding arginine as an isotonic agent to prepare the anti-IL-6 receptor antibody-containing formulation, aggregate generation was suppressed as compared to when using a sugar. It was also found that when aspartic acid and glutamic acid were used as counterion species, the effect of suppressing aggregates was higher than when hydrochloric acid was used. Furthermore, it was found that the generation of insoluble microparticles was suppressed by adding a specific concentration range of Poloxamer 188, which is a nonionic surfactant, to the antibody-containing solution, as compared to when another nonionic surfactant (Polysorbate 80) was added.

In one non-limiting embodiment, the present disclosure relates to a solution formulation comprising an anti-IL-6 receptor antibody as an active ingredient, said solution containing a histidine-aspartate buffer or histidine-glutamate buffer, Poloxamer 188, and arginine, and having a pH of 5.5 to 6.6. The solution formulations of the present disclosure include solution formulations which are not reconstituted solutions of lyophilized formulations, and solutions obtained after reconstituting lyophilized formulations. In a particular embodiment, the solution formulations of the present disclosure are solution formulations which are not reconstituted solutions of lyophilized formulations.

In another non-limiting embodiment, the present disclosure relates to a lyophilized formulation comprising an anti-IL-6 receptor antibody as an active ingredient, said formulation containing a histidine-aspartate buffer or a histidine-glutamate buffer, Poloxamer 188, and arginine, and having a pH of 5.5 to 6.6 after reconstitution in water.

In a specific embodiment, the formulations of the present disclosure comprise an aspartate or glutamate of a basic amino acid (e.g., histidine and/or arginine) and are substantially free of chloride and acetate ions. In a specific embodiment, the formulations of the present disclosure are substantially free of sugars. In the context of the formulations of the present disclosure, the sugars are, for example, sucrose, trehalose, meglumine, and sorbitol. "Substantially free" in relation to the formulations of the present disclosure means not containing in an amount to function as an ingredient in the formulations. In a specific embodiment, the osmotic pressure ratio of the formulations of the present disclosure is 0.9 to 1.3 (ratio to a saline solution).

In a specific embodiment, the generation of antibody aggregates (e.g., dimerization) in the formulations of the present disclosure is suppressed (e.g., reduced or inhibited). In a specific embodiment, the generation of foreign matter (e.g., insoluble particles, insoluble visible particles) in the formulations of the present disclosure is suppressed. In a specific embodiment, the formulations of the present disclosure are for subcutaneous administration. In a specific embodiment, the formulations of the present disclosure are stable at 2 to 8° C. for at least 6 months. In a specific embodiment, the proportion of aggregates in the formulations of the present disclosure is 2.0% or less, 1.8% or less, 1.6% or less, 1.4% or less, 1.2% or less, 1.0% or less, 0.8% or less, 0.7% or less, 0.6% or less, or 0.5% or less, at 2 to 8° C. over a period of at least 6 months, at least 9 months, at least 12 months, at least 15 months, at least 18 months, at least 24 months, or at least 30 months. In a specific embodiment, the formulations of the present disclosure have the proportion of aggregates of 2.0% or less, 1.8% or less, 1.6% or less, 1.4% or less, 1.2% or less, 1.0% or less, 0.9% or less, 0.8% or less, or 0.7% or less, at 25° C. over a period of at least 1 month, at least 3 months, or at least 6 months. In a specific embodiment, the percentage of insoluble particles (e.g., insoluble visible particles) generated in the formulations of the present disclosure is 25% or less, 20% or less, 15% or less, 10% or less, 7% or less, 6% or less, 5% or less, 4% or less, 3% or less, 2% or less, 1% or less, or 0.5% or less, at 2 to 8° C. over a period of at least 1 month, at least 3 months, at least 6 months, at least 9 months, at least 12 months, at least 18 months, or at least 24 months.

In one non-limiting embodiment, the formulations of the present disclosure comprise a histidine buffer as a buffer. The histidine is preferably L-histidine. In the formulations of the present disclosure, histidine may be included as a salt, and examples of such salts include histidine-hydrochloride, histidine-aspartate, and histidine-glutamate. When histidine is expressed by weight (for example, mg), those skilled in the art would understand that the weight may be the weight of histidine alone or the weight of histidine contained in a salt containing histidine. Furthermore, in the present disclosure, the weight or concentration of histidine may be the sum of the weight or concentration of histidine alone, and the weight or concentration of histidine contained in a salt containing histidine.

In one non-limiting embodiment, the formulations of the present disclosure comprise arginine as an isotonic agent. The arginine is preferably L-arginine. In the formulations of the present disclosure, arginine may be included as a salt, and examples of such salts include arginine-hydrochloride, arginine-aspartate, and arginine-glutamate. When arginine is expressed by weight (for example, mg), those skilled in the art would understand that the weight may be the weight of arginine alone or the weight of arginine contained in a salt containing arginine. Furthermore, in the present disclosure, the weight or concentration of arginine may be the sum of the weight or concentration of arginine alone and the weight or concentration of arginine contained in a salt containing arginine.

In one non-limiting embodiment, the formulations of the present disclosure comprise aspartic acid and/or glutamic acid as a counterion. Aspartic acid and glutamic acid are preferably L-aspartic acid and L-glutamic acid, respectively. In the formulations of the present disclosure, aspartic acid and glutamic acid may be included as salts, and examples of such salts include histidine-aspartate, arginine-aspartate, histidine-glutamate, and arginine-glutamate. When aspartic acid and glutamic acid are expressed by weight (for example, mg), those skilled in the art would understand that the weight may be the weight of the amino acid alone or the weight of the amino acid contained in a salt containing the amino acid. Furthermore, in the present disclosure, the weight or concentration of aspartic acid or glutamic acid may be the sum of the weight or concentration of the amino acid alone and the weight or concentration of the amino acid contained in a salt containing the amino acid.

In one non-limiting embodiment, the formulations of the present disclosure further comprise Poloxamer 188 as a nonionic surfactant. Poloxamer 188 may be referred to as "polyoxyethylene (160) polyoxypropylene (30) glycol" in the Japanese Pharmacopoeia standards.

The amount and concentration of an anti-IL-6 receptor antibody comprised in the formulations of the present disclosure are not particularly limited, and can be appropriately adjusted depending on a subject for administration, for example, whether it is for an adult or for a child, depending on whether it is for prophylaxis or for treatment, or depending on the type or severity and such of the disease or symptoms to be prevented or treated. Therefore, the molar ratio and the weight ratio of an anti-IL-6 receptor antibody contained in a formulation of the present disclosure to other components can take various values. In one non-limiting embodiment, the concentration in solution state of an anti-IL-6 receptor antibody contained in a formulation of the present disclosure (i.e., the concentration in a solution formulation, the concentration in a solution for a lyophilized formulation prior to lyophilization, or the concentration in a solution after reconstitution of a lyophilized formulation) is 10 to 500 mg/mL, for example 50 to 250 mg/mL, 60 to 200 mg/mL, 100 to 200 mg/mL, 120 to 200 mg/mL, 180 to 200 mg/mL, for example, 60 mg/mL, 100 mg/mL, 120 mg/mL, 180 mg/mL, or 200 mg/mL.

In one non-limiting embodiment, the concentration in solution state of the histidine buffer (e.g., histidine-aspartate buffer or histidine-glutamate buffer) contained in the formulations of the present disclosure is 1 to 500 mM (mmol/L), for example, 10 to 100 mM, 10 to 40 mM, for example, 20 mM.

In one non-limiting embodiment, the concentration in solution state of Poloxamer 188 contained in the formulations of the present disclosure is 0.06 to 5.0 mg/mL, such as 0.1 to 2.0 mg/mL, 0.15 to 1.0 mg/mL, 0.2 to 0.5 mg/mL, for example, 0.2 mg/mL or 0.5 mg/mL.

In one non-limiting embodiment, the concentration in solution state of arginine and/or a salt thereof contained in the formulations of the present disclosure is 3 to 500 mM (mmol/L), for example, 5 to 300 mM, 10 to 200 mM, 50 to 150 mM, for example, 50 mM, 100 mM, or 150 mM.

In one non-limiting embodiment, the pH of the formulations of the present disclosure in solution state is 5.2 to 6.9, for example, 5.5 to 6.6, 5.8 to 6.2, for example, 5.5, 6.0, or 6.3.

In one non-limiting embodiment, a formulation of the present disclosure is a solution formulation which comprises:

10 to 500 mg/mL of an anti-IL-6 receptor antibody,
 1 to 500 mM of a histidine-aspartate buffer or histidine-glutamate buffer,
 0.06 to 5.0 mg/mL of Poloxamer 188, and
 3 to 500 mM of arginine, and
 which has a pH of 5.2 to 6.9.

In a specific embodiment, a solution formulation of the present disclosure comprises:

50 to 250 mg/mL of an anti-IL-6 receptor antibody,
10 to 100 mM of a histidine-aspartate buffer or histidine-glutamate buffer,
0.1 to 2.0 mg/mL of Poloxamer 188, and
5 to 300 mM of arginine,
and has a pH of 5.5 to 6.6.

In a specific embodiment, a formulation of the present disclosure is a formulation for injection comprising:

(i) container (e.g., a vial, cartridge or syringe); and
(ii) an antibody solution formulation in the container which contains, per 1 mL of solution,
50 to 250 mg of an anti-IL-6 receptor antibody,
0.9 to 52.3 mg of L-arginine,
1.6 to 15.5 mg of L-histidine,
0.1 to 2.0 mg of Poloxamer 188, and
L-aspartic acid or L-glutamic acid, and
which has a pH of 5.5 to 6.6.

In a specific embodiment, a formulation of the present disclosure is a solution formulation for injection comprising:

(i) container (e.g., a vial, cartridge or syringe); and
(ii) an antibody solution formulation in the container which contains, per 1 mL of solution,
60 to 200 mg of an anti-IL-6 receptor antibody,
8.7 to 26.1 mg of L-arginine,
1.6 to 6.2 mg of L-histidine,
0.15 mg to 1.0 mg of Poloxamer 188, and
L-aspartic acid or L-glutamic acid, and
which has a pH of 5.5 to 6.3.

In a specific embodiment, a formulation of the present disclosure is a solution formulation for injection comprising:

(i) container (e.g., a vial, cartridge or syringe); and
(ii) an antibody solution formulation in the container which contains, per 1 mL of solution,
120 mg of an anti-IL-6 receptor antibody,
26.1 mg of L-arginine,
3.1 mg of L-histidine,
0.5 mg of Poloxamer 188, and
L-aspartic acid or L-glutamic acid, and
which has a pH of 5.8 to 6.2.

In another non-limiting embodiment, a formulation of the present disclosure is a lyophilized formulation which is a composition made by lyophilizing a solution comprising:

10 to 500 mg/mL of an anti-IL-6 receptor antibody,
1 to 500 mM of a histidine-aspartate buffer or histidine-glutamate buffer,
0.06 to 5.0 mg/mL of Poloxamer 188, and
3 to 500 mM of arginine,
wherein the pH after being reconstituted in water is 5.2 to 6.9.

In a specific embodiment, a lyophilized formulation of the present disclosure is a composition made by lyophilizing a solution comprising:

50 to 250 mg/mL of an anti-IL-6 receptor antibody,
10 to 100 mM of a histidine-aspartate buffer or histidine-glutamate buffer,
0.1 to 2.0 mg/mL of Poloxamer 188, and
5 to 300 mM of arginine,
wherein the pH after being reconstituted in water is 5.5 to 6.6.

In a specific embodiment, a formulation of the present disclosure is a formulation for injection comprising:

(i) a container (e.g., a vial, cartridge or syringe); and
(ii) a lyophilized formulation which is a composition made by lyophilizing a solution containing, per container:

50 to 250 mg of an anti-IL-6 receptor antibody,
0.9 to 52.3 mg of L-arginine,
1.6 to 15.5 mg of L-histidine,
0.1 to 2.0 mg of Poloxamer 188, and
L-aspartic acid or L-glutamic acid,
wherein the pH after reconstituted in water is 5.5 to 6.6.

In a specific embodiment, the formulations of the present disclosure contain, per syringe (1 mL):

120 mg of an anti-IL-6 receptor antibody (e.g., satralizumab),
26.1 mg of L-arginine,
3.1 mg of L-histidine,
0.5 mg of Poloxamer 188, and
L-aspartic acid or L-glutamic acid as a counterion,
wherein the pH in solution state is 5.8 to 6.2.

In the above embodiment, in the description of the numerical value, the numerical value of the smallest digit (for example, one digit) includes the numerical value obtained by rounding off the next lower digit (for example, if the smallest digit is one digit, the first decimal place). The formulations can also be expressed as containing, per syringe (1 mL):

120 mg (119.5 to 120.4 mg) of an anti-IL-6 receptor antibody (e.g., satralizumab),
26.1 mg (26.05 to 26.14 mg) of L-arginine,
3.1 mg (3.05 to 3.14 mg) of L-histidine,
0.5 mg (0.45 to 0.54 mg) of Poloxamer 188, and
L-aspartic acid or L-glutamic acid as a counterion.

In one non-limiting embodiment, the present disclosure relates to a formulation for injection or a kit, comprising (i) a container; and (ii) a solution formulation of the present disclosure.

In one non-limiting embodiment, the disclosure relates to a formulation for injection or a kit, comprising (i) a container; (ii) a lyophilized formulation of the present disclosure; and (iii) optionally, water for injection to reconstitute the lyophilized formulation. In one embodiment, the container of the formulations for injection or kits of the present disclosure is a plastic or glass syringe, cartridge, or vial. Preferably, the container of formulations for injection of the present disclosure is a plastic syringe. Specific examples thereof include resins such as cycloolefin-based resins, polyethylene resins and polypropylene resins, and particularly preferably, cycloolefin-based resin such as COP (Cyclic Olefin Polymer) and COC (Cyclic Olefin Copolymer). Such syringes are particularly suitable for use as syringes for filling tray fillers used in mass production in industrial manufacturing.

More preferably, the container of formulations for injection of the present disclosure is a plastic syringe with a needle. The material of the needle cap of the formulations for injection of the present disclosure needs to be a material that can be attached to and detached from the syringe body, can be tightly closed against the syringe body, has elasticity, and has low water vapor permeability, which specifically includes butyl rubber (IIR) and the like. The butyl rubber may be a halogenated butyl rubber such as bromobutyl rubber (BIIR) or chlorobutyl rubber (CIIR) in addition to normal butyl rubber. As for the structure of the cap, there is no restriction as long as the above-mentioned material is formed into a tubular shape with one end being closed and the other end having an opening that can be attached by closely surrounding the outer circumference of the injection needle or the syringe body. It may be single layered, multi-layered, or be any other structure. Further, the inside of the opening may be provided with grooves or protrusions for attaching/detaching the cap. The cap may be attached so as to cover from the needle tip to one end of the outer cylinder which is the syringe body, or may be attached so as to cover from the needle tip to the connector portion between the injection needle and the syringe body.

In a particular embodiment, the container of formulations for injection or kits of the present disclosure is a dual chamber syringe (DCS) or dual chamber cartridge (DCC), and a lyophilized formulation and water for injection are enclosed in separate compartments in the container, i.e., the lyophilized formulation of the present disclosure is filled into either one of two chambers and water for injection is filled into the other chamber. Preferably, water for injection is water, and optionally satisfies the standards of "water for injection" specified in the Pharmacopoeia of Japan.

If needed, the formulations of the present invention may additionally contain appropriate cryoprotectants, suspending agents, solubilizing agents, tonicity agents, preservatives, adsorption inhibitors, diluents, excipients, pH adjustors, analgesics, sulfur-containing reducing agents, antioxidants, and such.

In one non-limiting embodiment, the present disclosure is a method of stabilizing an antibody in a formulation comprising an anti-IL-6 receptor antibody (for example, a solution formulation), which comprises the step of adding L-aspartic acid or L-glutamic acid (as a counterion). In another non-limiting embodiment, the present disclosure relates to a method of suppressing antibody association (e.g., dimerization) in a formulation comprising an anti-IL-6 receptor antibody (e.g., a solution formulation), comprising the step of adding L-aspartic acid or L-glutamic acid (as a counterion). The present disclosure relates to a method of suppressing the generation of foreign matter and insoluble particles in a formulation comprising an anti-IL-6 receptor antibody (for example, a solution formulation), which comprises the step of adding L-aspartic acid or L-glutamic acid (as a counterion). In a certain embodiment, the method of the present disclosure further comprises the step of adding Poloxamer 188 to a concentration in solution of 0.1 to 2.0 mg/mL. In a certain embodiment, the insoluble particles are insoluble visible particles.

In the present invention, the term "stable antibody-containing formulation" refers to a formulation in which aggregates and/or insoluble particles from proteins such as antibodies are difficult to be generated, i.e., the formulations in which deterioration reactions, including generation of insoluble aggregates, soluble aggregates, or other insoluble particles, are difficult to occur in the formulation.

Further, in the present specification, "method of stabilizing a solution comprising an antibody" refers to a method that makes it difficult for proteins such as antibodies to generate aggregates and/or insoluble particles in the solutions, and the method includes methods of suppressing the association of antibodies, methods of suppressing dimerization of antibodies, and methods of suppressing the generation of insoluble particles in solutions comprising an antibody.

As used herein, the term "association" refers to a state in which two or more components (e.g., a polypeptide or antibody) in, for example, a composition (e.g., an antibody-containing formulation, an antibody-containing solution) interact with each other, an example being dimerization. In the present invention, "suppressing association", "suppressing aggregates", "suppressing aggregate generation", and "suppressing aggregate formation" are used interchangeably, and refers to suppressing self-association of components (for example, polypeptides, for example, antibodies)

comprised in a composition (for example, an antibody-containing formulation, antibody-containing solution).

In the context of the antibody-containing formulations (solution formulations or lyophilized formulations) of the present disclosure, "association (e.g., dimerization) of the antibodies is suppressed" and "association of the antibodies (e.g., dimerization) is reduced" are used interchangeably, and it means that the association (for example, dimerization) of the antibodies during storage of the formulations in a solution state or a frozen state is suppressed. It suffices if there are fewer antibody aggregates (e.g., dimers) in the formulations compared to when at least one of the components of the formulations is not contained (at a given concentration), and encompasses "association (e.g., dimerization) is inhibited". As used herein, "association (e.g., dimerization) is suppressed (reduced or inhibited)" means that association (e.g., dimerization) is reduced by at least 10%, 20%, 30%, 40%, 50%, 60%, 70%, 80%, 90%, 95%, or 100%.

Aggregates include insoluble aggregates, soluble aggregates, etc., and aggregates are synonymous with HMWS (high molecular weight substance species). Major aggregates are dimers. Amounts of aggregates can be measured by size exclusion chromatography (SEC), SDS polyacrylamide gel electrophoresis (SDS-PAGE), capillary SDS gel electrophoresis (CE-SDS), dynamic light scattering (DLS), light obscuration automated microparticle counter (HIAC), flow imaging, Analytical Ultracentrifuge (AUC) and such, and measurements by size exclusion chromatography (SEC) are preferred in the present invention. It is thought that as measurement conditions, samples are measured using a column (TOSOH, TSKgel G3000SWXL), using 50 mmol/L phosphate buffer (pH 7.0), 300 mmol/L sodium chloride, 0.05% sodium azide as a mobile phase at a flow rate of 0.5 mL/min, but conditions are not limited thereto. In one embodiment, amounts of aggregates are measured by the methods described in Examples herein.

In the context of the antibody-containing formulations (solution formulations or lyophilized formulations) of the present disclosure, "foreign matter generation is suppressed" means that foreign matter generation during storage of the formulations in a solution state or a frozen state is suppressed. It suffices if the generation of foreign matter in the formulations is less than when at least one of the components of the formulations is not contained (at a given concentration), and encompasses the suppression of the generation of insoluble particles (for example, insoluble visible particles). As used herein, "foreign matter generation is suppressed" means that foreign matter generation is reduced by at least 10%, 20%, 30%, 40%, 50%, 60%, 70%, 80%, 90%, 95%, or 100%.

Foreign matter includes insoluble particles and the like, and insoluble particles include insoluble microparticles such as insoluble aggregates, and insoluble visible particles. Insoluble particles can be measured by a known visual inspection instrument (Japanese Pharmacopoeia 17th Edition, General Tests, 6. Tests for Formulations, 6.06 Foreign Insoluble Matter Test for Injections), and such, for example, by a method described in the Examples of the present specification, but it is not limited thereto.

[Anti-IL-6 Receptor Antibodies]

Anti-IL-6 receptor antibodies used in the present invention inhibit the binding of IL-6 to the IL-6 receptor by binding to the IL-6 receptor, and blocks the transduction of the biological activity of IL-6 into the cells. An example of such anti-IL-6 receptor antibodies is an antibody comprising a heavy chain variable region which contains a CDR1 having the sequence of SEQ ID NO: 1 (heavy chain CDR1 of SA237), a CDR2 having the sequence of SEQ ID NO: 2 (heavy chain CDR2 of SA237), and a CDR3 having the sequence of SEQ ID NO: 3 (heavy chain CDR3 of SA237), and a light chain variable region which contains a CDR1 having the sequence of SEQ ID NO: 4 (light chain CDR1 of SA237), a CDR2 having the sequence of SEQ ID NO: 5 (SA237 light chain CDR2), and a CDR3 having the sequence of SEQ ID NO: 6 (SA237 light chain CDR3). The antibodies may be a full-length antibody or an antibody fragment, and are preferably an IgG type (for example, IgG1, IgG2, IgG3, IgG4) antibody. The antibodies are, preferably, an antibody comprising the heavy chain variable region of SEQ ID NO: 8 (heavy chain variable region of SA237) and the light chain variable region of SEQ ID NO: 7 (light chain variable region of SA237), more preferably, an antibody comprising a heavy chain which contains the sequence of SEQ ID NO: 10 (heavy chain of SA237) and a light chain which contains the sequence of SEQ ID NO: 9 (light chain of SA237), and particularly preferably, SA237 (satralizumab).

The term "antibody" used herein is used in the broadest sense, and includes monoclonal antibodies, polyclonal antibodies, dimers, multimers, multispecific antibodies (such as bispecific antibodies), antibody fragments, antibody derivatives, and modified antibodies (Miller K et al. J Immunol. 2003, 170(9), 4854-61) so long as they show a desired biological activity. The antibodies may be mouse antibodies, human antibodies, humanized antibodies, chimeric antibodies, or those derived from another species, or artificially synthesized antibodies. The antibodies disclosed herein can be of any type (for example, IgG, IgE, IgM, IgD, and IgA), class (for example, IgG1, IgG2, IgG3, IgG4, IgA1 and IgA2) or subclass of immunoglobulin molecules. The immunoglobulins can be derived from any species (for example, human, mouse, or rabbit). The terms "antibody", "immune globulin" and "immunoglobulin" are used interchangeably in a broad sense.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments.

Recombinant antibodies produced by using genetic engineering techniques can be used as the antibodies. A recombinant antibody can be obtained by cloning a DNA encoding the antibody from hybridomas or antibody-producing cells such as sensitized lymphocytes that produce antibodies; inserting this into a vector; and then introducing it into hosts (host cells) to produce the antibody.

Antibodies of the present invention can be produced by methods known to those skilled in the art. Specifically, a DNA encoding the antibody of interest is inserted into an expression vector. The insertion into the expression vector is carried out such that the expression will take place under the control of expression regulatory regions such as an enhancer and a promoter. Next, host cells are transformed using this expression vector to express the antibody. Appropriate combinations of a host and an expression vector can be used in this case.

The antibodies of the present invention thus obtained can be isolated from the inside of host cells or the outside of the cells (medium, etc.), and purified to be substantially pure, homogeneous antibodies. The antibodies can be separated and purified by methods ordinarily used for separating and purifying antibodies, and the methods are not limited in any way. For example, the antibodies can be separated and purified by appropriately selecting and combining column chromatography, filtration, ultrafiltration, salting-out, solvent precipitation, solvent extraction, distillation, immuno-precipitation, SDS-polyacrylamide gel electrophoresis, iso-electrofocusing, dialysis, recrystallization, and such.

Known methods for defining CDRs include the method according to Kabat et al. (Sequences of Proteins of Immunological Interest, 5th Ed (1991), Bethesda, MD), the method according to Chothia et al. (Science (1986) 233, 755-758), and the method based on antigen-antibody contact regions (J Mol Biol (1996) 262, 732-745). Specifically, each of the methods defines CDRs as follows:

| CDR | Kabat | Chothia | Contact |
|-----|-------|---------|---------|
| L1 | L24-L34 | L24-L34 | L30-L36 |
| L2 | L50-L56 | L50-L56 | L46-L55 |
| L3 | L89-L97 | L89-L97 | L89-L96 |
| H1 | H31-H35B | H26-H32/34 | H30-H35B (Kabat numbering |
| H1 | H31-H35 | H26-H32 | H30-H35 (Chothia numbering) |
| H2 | H50-H65 | H52-H56 | H47-H58 |
| H3 | H95-H102 | H95-H102 | H93-H101 |

[Uses of the Antibody-Containing Formulations]

In a non-limiting embodiment, the formulations of the present disclosure can be used to prevent and/or treat IL-6-related diseases or resulting symptoms.

In one non-limiting embodiment, the present disclosure relates to a formulation (pharmaceutical composition), i.e., a solution formulation and lyophilized formulation which is a pharmaceutical composition for preventing and/or treating an IL-6-related disease comprising an anti-IL-6 receptor antibody as an active ingredient, which comprises 10 to 500 mg/mL (for example, 50 to 250 mg/mL) of an anti-IL-6 receptor antibody, 1 to 500 mM (for example, 10 to 100 mM) of a histidine-aspartate buffer or histidine-glutamate buffer, 0.06 to 5.0 mg/mL (e.g., 0.1 to 2.0 mg/mL) of Poloxamer 188, and 3 to 500 mM (e.g., 5-300 mM) of arginine, wherein the pH in solution state is 5.2 to 6.9 (for example, 5.5 to 6.6).

The preferable administration schedule of an antibody-containing formulation (pharmaceutical composition) of the present disclosure can be adjusted such as by appropriately extending the administration interval while monitoring the medical condition and the tendencies of the blood test values. In a specific embodiment, an antibody-containing formulation (pharmaceutical composition) of the present disclosure is administered as usual, after a short-interval administration period in which the same dose as a usual dose (e.g., antibody 120 mg/dose) is administered at an interval shorter (e.g., 2-week interval) than the normal dosing interval (e.g., 4-week interval) as described, for example, in WO2016/136933.

The antibody-containing formulations of the present invention can be administered to a patient via any appropriate route, for example, by bolus injection or continuous infusion for a certain period, intravenously, intramuscularly, or subcutaneously. In certain embodiments, the antibody-containing formulations of the present invention is administered via intravenous administration or subcutaneous administration. In certain embodiments, the antibody-containing formulations of the present invention is for subcutaneous administration.

In the present invention, "IL-6-related disease" refers to a disease related to IL-6, and examples include rheumatoid arthritis, juvenile idiopathic arthritis, systemic-onset juvenile idiopathic arthritis, Castleman's disease, systemic lupus erythematosus (SLE), lupus nephritis, Crohn's disease, lymphoma, ulcerative colitis, anemia, vasculitis, Kawasaki disease, Still's disease, amyloidosis, multiple sclerosis, transplantation, age-related macular degeneration, ankylosing spondylitis, psoriasis, psoriatic arthritis, chronic obstructive pulmonary disease (COPD), IgA nephropathy, osteoarthritis, asthma, diabetic nephropathy, GVHD, endometriosis, hepatitis (NASH), myocardial infarction, arteriosclerosis, sepsis, osteoporosis, diabetes, multiple myeloma, prostate cancer, kidney cancer, B-cell non-Hodgkin's lymphoma, pancreatic cancer, lung cancer, esophageal cancer, colon cancer, cancer cachexia, cancer nerve invasion, myopic choroidal neovascularization, idiopathic choroidal neovascularization, uveitis, chronic thyroiditis, delayed hypersensitivity, contact dermatitis, atopic dermatitis, mesothelioma, polymyositis, dermatomyositis, panuveitis, anterior uveitis, intermediate uveitis, scleritis, keratitis, orbital inflammation, optic neuritis, diabetic retinopathy, proliferative vitreoretinopathy, dry eye, post-operative inflammation, neuromyelitis optica (NMO), neuromyelitis optica spectrum disorder (NMOSD), myasthenia gravis, and pulmonary hypertension.

In one non-limiting embodiment, the present disclosure relates to an anti-IL-6 receptor antibody for use in the prevention and/or treatment of an IL-6-related disease, characterized by being used as a solution formulation which comprises 10 to 500 mg/mL (e.g., 50 to 250 mg/mL) of anti-IL-6 receptor antibody, 1 to 500 mM (e.g., 10 to 100 mM) of a histidine-aspartate buffer or histidine-glutamate buffer, 0.06 to 5.0 mg/mL (e.g., 0.1 to 2.0 mg/mL) of Poloxamer 188, and 3 to 500 mM (for example 5 to 300 mM) of arginine, and which has a pH of 5.2 to 6.9 (for example 5.5 to 6.6).

In one non-limiting embodiment, the present disclosure relates to an anti-IL-6 receptor antibody for use in the prevention and/or treatment of an IL-6-related disease, characterized by being used after redissolving a lyophilized formulation in which a solution comprising 10 to 500 mg/mL (e.g., 50 to 250 mg/mL) of an anti-IL-6 receptor antibody, 1 to 500 mM (e.g., 10 to 100 mM) of a histidine-aspartate buffer or histidine-glutamate buffer, 0.06 to 5.0 mg/mL (e.g., 0.1 to 2.0 mg/mL) of Poloxamer 188, and 3 to 500 mM (e.g., 5 to 300 mM) of arginine, and having a pH of 5.2 to 6.9 (for example, 5.5 to 6.6), is lyophilized.

In one non-limiting embodiment, the present disclosure relates to a method of preventing and/or treating an IL-6-related disease, wherein the method comprises administering a solution formulation to a subject who has or is at risk of having an IL-6-related disease, wherein the solution formulation comprises 10 to 500 mg/mL (e.g., 50 to 250 mg/mL) of an anti-IL-6 receptor antibody, 1 to 500 mM (e.g., 10 to 100 mM) of a histidine-aspartate buffer or histidine-glutamate buffer, 0.06 to 5.0 mg/mL (e.g., 0.1 to 2.0 mg/mL) of Poloxamer 188, and 3 to 500 mM (e.g., 5 to 300 mM) of arginine, and has a pH of 5.2 to 6.9 (e.g., 5.5 to 6.6).

In one non-limiting embodiment, the present disclosure relates to a method of preventing and/or treating an IL-6-related disease, wherein the method comprises: preparing a lyophilized formulation by lyophilizing a solution which comprises 10 to 500 mg/mL (e.g., 50 to 250 mg/mL) of an anti-IL-6 receptor antibody, 1 to 500 mM (e.g., 10 to 100 mM) of a histidine-aspartate buffer or histidine-glutamate buffer, 0.06 to 5.0 mg/mL (e.g., 0.1 to 2.0 mg/mL) of Poloxamer 188, and 3 to 500 mM (e.g., 5 to 300 mM) of arginine, and which has a pH of 5.2 to 6.9 (e.g., 5.5 to 6.6); redissolving the lyophilized formulation to prepare a redissolved solution; and administering the redissolved solution to the subject who has or is at risk of having an IL-6-related disease.

As used herein, the "subject" may preferably be an animal, and more preferably a mammal (a mouse, a rat, a rabbit, a dog, a monkey (e.g., a cynomolgus monkey), or the like), and particularly preferably a human, but not limited thereto. The human may be an adult (18 years or older) or a child (0 to younger than 18 years, for example, 6 months to younger than 18 years).

In one non-limiting embodiment, the present disclosure relates to the use of an anti-IL-6 receptor antibody in the manufacture of a medicament for the prevention and/or treatment of an IL-6-related disease, characterized by preparing a solution formulation which comprises 10 to 500 mg/mL (e.g., 50 to 250 mg/mL) of an anti-IL-6 receptor antibody, 1 to 500 mM (e.g., 10 to 100 mM) of a histidine-aspartate buffer or histidine-glutamate buffer, 0.06 to 5.0 mg/mL (e.g., 0.1 to 2.0 mg/mL) of Poloxamer 188, and 3 to 500 mM (e.g., 5 to 300 mM) of arginine, and which has a pH of 5.2 to 6.9 (e.g., 5.5 to 6.6).

In one non-limiting embodiment, the present disclosure relates to the use of an anti-IL-6 receptor antibody in the manufacture of a medicament for the prevention and/or treatment of an IL-6-related disease, characterized by preparing a lyophilized formulation by lyophilizing a solution which comprises 10 to 500 mg/mL (e.g., 50 to 250 mg/mL) of an anti-IL-6 receptor antibody, 1 to 500 mM (e.g., 10 to 100 mM) of a histidine-aspartate buffer or histidine-glutamate buffer, 0.06 to 5.0 mg/mL (e.g., 0.1 to 2.0 mg/mL) of Poloxamer 188, and 3 to 500 mM (e.g., 5 to 300 mM) of arginine, and which has a pH of 5.2 to 6.9 (e.g., 5.5 to 6.6).

As used herein, aspects referred to by the expression "comprising" include those referred to by the expression "essentially consisting of", and those referred to by the expression "consisting of".

Numerical values recited herein may vary within a certain range, for example, depending on the instruments or equipment, measurement conditions, and procedure used by those skilled in the art, and so long as they are within a range that allows the objective of the invention to be accomplished, they may encompass a deviation of approximately 10%, for example.

All patents and references explicitly cited herein are incorporated by reference into this specification in its entirety.

The present invention will be further illustrated by the Examples below, but it is not to be construed as being limited thereto.

EXAMPLES

[Example 1] Effect of pH and Histidine Buffer on Suppressing Increase in Aggregates During a Severe Heat Test and a Freeze-Thaw Test of Satralizumab

[1-1] Stability Evaluation of Satralizumab Formulations in a Severe Test
(1) Material
Satralizumab is a humanized anti-IL-6 receptor monoclonal antibody for indications such as neuromyelitis optica in which the involvement of IL-6 is suggested.
(2) Test Samples
20 mmol/L L-histidine buffer and 20 mmol/L citrate buffer were prepared at pH 4.5, 5.0, 5.5, 6.0 and 6.3, respectively, for 100 mg/mL satralizumab and 150 mmol/L NaCl. The prepared drug solutions were allowed to stand in a thermostatic chamber at 40° C. for 2, 4 or 8 weeks, and used as test samples.

(3) Method of Measuring Aggregate Mass of Satralizumab

The aggregate mass was measured by size exclusion chromatography (SEC) of the samples at a flow rate of 0.5 mL/min, using a column (Tosoh, TSK Gel G3000SW×L) and 50 mmol/L phosphate buffer (pH 7.0) and 300 mmol/L potassium chloride as the mobile phase.

Of the peaks detected, the one with the largest area and height was taken as monomers, and the peaks detected before the monomers were collectively taken as aggregates (HMWS).

The area was calculated for all peaks, and the peak area ratio of the target peak was calculated according to the following formula.

$$\text{Peak area ratio of the target peak}(\%) = \frac{\text{Peak area of the target peak}}{\text{Peak area of the target peak} + \text{Total of other peak areas}} \times 100$$

(4) Results

The results obtained are shown in Table 1.

TABLE 1

| Type of buffer | | L-histidine buffer | | | | | Citrate buffer | | | | |
|---|---|---|---|---|---|---|---|---|---|---|---|
| pH | | 4.5 | 5.0 | 5.5 | 6.0 | 6.3 | 4.5 | 5.0 | 5.5 | 6.0 | 6.3 |
| HMWS | Initial | 2.31 | 1.54 | 1.00 | 0.99 | 0.98 | 1.37 | 0.98 | 0.96 | 0.97 | 1.00 |
| (%) | 2W | 64.89 | 8.46 | 2.08 | 2.00 | 1.95 | 84.37 | 21.64 | 2.09 | 2.20 | 2.29 |
| | 4W | 71.12 | 10.96 | 2.48 | 2.23 | 2.30 | 86.75 | 25.41 | 2.34 | 2.49 | 2.66 |
| | 8W | 82.31 | 17.10 | 4.07 | 3.35 | 3.29 | 93.14 | 35.57 | 3.84 | 3.75 | N/A |

N/A: The measurement could not be performed because the drug solution evaporated during storage.

As is clear from Table 1, pH 4.5 and 5.0 showed a significant increase in aggregates compared to pH 5.5, 6.0 and 6.3. In addition, at pH 5.5, 6.0 and 6.3, the L-histidine buffer solution showed a better aggregate suppression effect than the citrate buffer solution.

[1-2] Stability Evaluation of Satralizumab Formulations in a Freeze-Thaw Test (1) Material The antibody described in Example 1-1 was used.

(2) Test Samples 20 mmol/L L-histidine buffer and 20 mmol/L citrate buffer were prepared at pH 4.5, 5.0, 5.5, 6.0 and 6.3, respectively, for 100 mg/mL satralizumab and 150 mmol/L NaCl. The prepared drug solutions were freeze-thawed (−20° C./room temperature, 5 cycles and 10 cycles) and used as test samples.

(3) Method of Measuring Aggregate Mass of Satralizumab

The method described in Example 1-1 was followed.

(4) Result

The results obtained are shown in Table 2.

TABLE 2

| Type of buffer | | L-histidine buffer | | | | | Citrate buffer | | | | |
|---|---|---|---|---|---|---|---|---|---|---|---|
| pH | | 4.5 | 5.0 | 5.5 | 6.0 | 6.3 | 4.5 | 5.0 | 5.5 | 6.0 | 6.3 |
| HMWS | Initial | 2.31 | 1.54 | 1.00 | 0.99 | 0.98 | 1.37 | 0.98 | 0.96 | 0.97 | 1.00 |
| (%) | 5 cycles | 2.94 | 1.51 | 1.15 | 1.05 | 1.13 | 2 68 | 1.27 | 1.23 | 1.14 | 1.11 |
| | 10 cycles | 2.77 | 1.27 | 1.02 | 0.98 | 1.04 | 2.51 | 1.01 | 1.02 | 1.03 | 0.98 |

[Example 2] Effect of L-Arginine on Suppressing Increase in Aggregates During a Severe Heat Test and a Freeze-Thaw Test of Satralizumab

[2-1] Stability evaluation of satralizumab formulations in a severe test (1) Material The antibody described in Example 1-1 was used.

(2) Test Sample

Drug solutions with a pH of 6.5 were prepared by adding 100 mmol/L L-arginine, 100 mmol/L sucrose, and 100 mmol/L trehalose to 100 mg/mL satralizumab, 20 mmol/L L-histidine/hydrochloric acid buffer, and 50 mmol/L NaCl. The prepared drug solutions were allowed to stand in a thermostatic chamber at 40° C. for 2, 4 or 8 weeks, and used as test samples.

(3) Method of Measuring Aggregate Mass of Satralizumab

The aggregate mass was measured by size exclusion chromatography (SEC) of the samples at a flow rate of 0.5 mL/min using a column (Tosoh, TSK Gel G3000SW×L), and 50 mmol/L phosphate buffer (pH 7.0) and 300 mmol/L sodium chloride as the mobile phase.

Of the peaks detected, the one with the largest area and height was taken as monomers, and the peaks detected before the monomers were collectively taken as aggregates (HMWS).

The area was calculated for all peaks, and the peak area ratio of the target peak was calculated according to the following formula.

Peak area ratio of the target peak (%) =

1p;.5p $$\frac{\text{Peak area of the target peak}}{\text{Peak area of the target peak} + \text{Total of other peak areas}} \times 100$$

(4) Result

The results obtained are shown in Table 3.

TABLE 3

| Type of isotonic agent | | None | L-arginine | Sucrose | Trehalose |
|---|---|---|---|---|---|
| HMWS | Initial | 0.80 | 0.80 | 0.81 | 0.79 |
| (%) | 2W | 2.21 | 1.79 | 2.04 | 2.16 |
| | 4W | 2.62 | 2.03 | 2.45 | 2.53 |
| | 8W | 3.59 | 2.76 | 3.42 | 3.21 |

As is clear from Table 3, the generation of aggregates was most suppressed by L-arginine.

[2-2] Stability Evaluation of Satralizumab Formulations in a Freeze-Thaw Test (1) Material The antibody described in Example 1-1 was used.

(2) Test Sample

Drug solutions with a pH of 6.5 were prepared by adding 100 mmol/L L-arginine, 100 mmol/L sucrose, and 100 mmol/L trehalose to 100 mg/mL satralizumab, 20 mmol/L L-histidine/hydrochloric acid buffer, and 50 mmol/L NaCl. The prepared drug solutions were freeze-thawed (−20° C./room temperature, 5 cycles and 10 cycles) and used as test samples.

(3) Method of Measuring Aggregate Mass of Satralizumab

The method described in Example 2-1 was followed.

(4) Result

The results obtained are shown in Table 4.

TABLE 4

| Type of isotonic agent | | None | L-arginine | Sucrose | Trehalose |
|---|---|---|---|---|---|
| HMWS | Initial | 0.80 | 0.80 | 0.81 | 0.79 |
| (%) | 5 cycles | 1.41 | 0.95 | 0.86 | 0.87 |
| | 10 cycles | 1.53 | 0.83 | 0.77 | 0.83 |

In the freeze-thaw test, no clear difference was observed between the isotonic agents.

[2-3] Severe Test and Stability Evaluation Under Recommended Storage Conditions for Satralizumab Formulations (1) Material The antibody described in Example 1-1 was used.

(2) Test Sample

Drug solutions with a pH of 6.0 were prepared by adjusting the L-arginine concentrations to 50 mmol/L, 100 mmol/L, and 150 mmol/L, with respect to 200 mg/mL satralizumab and 20 mmol/L L-histidine/hydrochloric acid buffer. The prepared drug solutions were allowed to stand in a thermostatic chamber at 40° C. for 2, 4 or 8 weeks, or in a thermostatic chamber at 5° C. for 3, 6, 12, 18 or 24 months, and used as test samples.

(3) Method of Measuring Aggregate Mass of Satralizumab

The method described in Example 1-1 was followed.

(4) Result

The obtained results are shown in Tables 5 and 6.

TABLE 5

| Stability test results at 40° C. | | | |
|---|---|---|---|
| L-arginine concentration | 50 mmol/L | 100 mmol/L | 150 mmol/L |
| HMWS Initial | 0.99 | 0.98 | 0.98 |
| (%) 2W | 2.49 | 2.35 | 2.22 |

TABLE 5-continued

| Stability test results at 40° C. | | | |
|---|---|---|---|
| L-arginine concentration | 50 mmol/L | 100 mmol/L | 150 mmol/L |
| 4W | 3.20 | 3.04 | 2.89 |
| 8W | 4.23 | 4.04 | 3.98 |

TABLE 6

| Stability test results at 5° C. | | | |
|---|---|---|---|
| L-arginine concentration | 50 mmol/L | 100 mmol/L | 150 mmol/L |
| HMWS | Initial | 0.99 | 0.98 | 0.98 |
| (%) | 3M | 1.23 | 1.17 | 1.11 |
| | 6M | 1.39 | 1.31 | 1.24 |
| | 12M | 1.54 | 1.45 | 1.38 |
| | 18M | 1.68 | 1.70 | 1.45 |
| | 24M | 2.04 | 1.68 | 1.59 |

As is clear from Tables 5 and 6, the generation of aggregates was most suppressed by the 150 mmol/L L-arginine prescription.

[2-4] Stability Evaluation of Satralizumab Formulations in a Freeze-Thaw Test (1) Material The antibody described in Example 1-1 was used.

(2) Test Sample

Drug solutions were prepared such that the L-arginine concentrations were 50 mmol/L, 100 mmol/L, and 150 mmol/L, with respect to 200 mg/mL satralizumab and 20 mmol/L L-histidine/hydrochloric acid buffer. The prepared pH 6.0 drug solutions were freeze-thawed (−20° C./room temperature, 5 cycles and 10 cycles) and used as test samples.

(3) Method of Measuring Aggregate Mass of Satralizumab

The method described in Example 2-1 was followed.

(4) Result

The results obtained are shown in Table 7.

TABLE 7

| L-arginine concentration | 50 mmol/L | 100 mmol/L | 150 mmol/L |
|---|---|---|---|
| HMWS | Initial | 0.99 | 0.98 | 0.98 |
| (%) | 5 cycles | 4.49 | 2.96 | 1.89 |
| | 10 cycles | 5.72 | 3.45 | 2.13 |

As is clear from Table 7, the increase in aggregates was most suppressed by the 150 mmol/L L-arginine prescription.

[Example 3] Effect of L-Aspartic Acid on the Suppression of Increase in Aggregates During an Accelerated Test and a Freeze-Thaw Test of Satralizumab

[3-1] Stability Evaluation of Satralizumab Formulations in an Accelerated Test (1) Material The antibody described in Example 1-1 was used.

(2) Test Sample

Drug solutions with a pH of 6.0 were prepared by adding 20 mmol/L L-histidine/hydrochloric acid, 20 mmol/L histidine/L-aspartic acid, and 20 mmol/L histidine/L-glutamic acid as buffer to 200 mg/mL satralizumab and 50 mmol/L arginine. The prepared drug solutions were allowed to stand in a thermostatic chamber at 25° C. for 2, 4 or 12 weeks, and used as test samples.

(3) Method of Measuring Aggregate Mass of Satralizumab

The method described in Example 2-1 was followed.

(4) Result

The results obtained are shown in Table 8.

TABLE 8

| Counterion species | | Hydrochloric acid (chloride ion) | L-aspartic acid | L-glutamic acid |
|---|---|---|---|---|
| HMWS | Initial | 1.29 | 1.28 | 1.25 |
| (%) | 2W | 1.71 | 1.58 | 1.55 |
| | 4W | 1.93 | 1.76 | 1.73 |
| | 12W | 2.35 | 2.12 | 2.06 |

As is clear from Table 8, L-aspartic acid and L-glutamic acid showed a better effect of suppressing aggregate generation than chloride ion.

[3-2] Stability Evaluation of Satralizumab Formulations in a Freeze-Thaw Test (1) Material The antibody described in Example 1-1 was used.

(2) Test Samples

Drug solutions with a pH of 6.0 were prepared by adding 20 mmol/L L-histidine/hydrochloric acid, 20 mmol/L histidine/L-aspartic acid, and 20 mmol/L histidine/L-glutamic acid as buffer to 200 mg/mL satralizumab and 50 mmol/L arginine. The prepared drug solutions were freeze-thawed (−20° C./room temperature, 5 cycles and 10 cycles) and used as test samples.

(3) Method of Measuring Aggregate Mass of Satralizumab

The method described in Example 2-1 was followed.

(4) Result

The results obtained are shown in Table 9.

TABLE 9

| Counterion species | | Hydrochloric acid (chloride ion) | L-aspartic acid | L-glutamic acid |
|---|---|---|---|---|
| HMWS | Initial | 1.29 | 1.28 | 1.25 |
| (%) | 5 cycles | 2.84 | 1.96 | 1.62 |
| | 10 cycles | 3.94 | 2.57 | 2.01 |

As is clear from Table 9, L-aspartic acid and L-glutamic acid showed a better effect of suppressing aggregate generation than chloride ion. Since L-glutamic acid is known to cause significant pain when administered subcutaneously, L-aspartic acid was considered to be preferable.

[Example 4] the Effect of Poloxamer 188 on the Suppression of Foreign Matter Generation During The Recommended Storage Conditions of Satralizumab

[4-1] Stability Evaluation of Satralizumab Formulations in a Recommended Storage Test (1) Material The antibody described in Example 1-1 was used.

(2) Test Samples 0.05 mg/mL Polysorbate 80 and 0.5 mg/mL Poloxamer 188 were added as surfactants to a drug solution of 180 mg/mL satralizumab, 20 mmol/L L-histidine/L-aspartate buffer, 150 mmol/L L-arginine, with a pH of 6.0, and filled into glass vials at 1.5 mL each. These filled drug solutions were allowed to stand in a thermostatic chamber at 5° C. for 1, 3, 6, 9, 12, 18, and 24 months and used as test samples.

(3) Method of Evaluating Insoluble Visible Particles in Test Samples

The samples were rotated using a visual inspection machine (Eisai APK03) until the sample liquid level reached the bottom of the vial. The rotation was stopped and a visual inspection was performed for 15 seconds per sample to confirm the presence or absence of insoluble visible particles.

(4) Result

The results obtained are shown in Table 10.

TABLE 10

| | 1M | 3M | 6M | 9M | 12M | 18M | 24M |
|---|---|---|---|---|---|---|---|
| Polysorbate 80 (number of vials among 30 vials in which insoluble visible particles were observed) | 0 | 19 | 6 | 9 | 28 | 28 | 28 |
| Poloxamer 188 (number of vials among 15 vials in which insoluble visible particles were observed) | 0 | 0 | 1 | 0 | 0 | 0 | 10 |

As is clear from Table 10, the generation of insoluble visible particles was suppressed in the Poloxamer 188 prescriptions compared to the Polysorbate 80 prescriptions.

[4-2] Stability Evaluation of Satralizumab Formulations in a Recommended Storage Test (1) Material The antibody described in Example 1-1 was used.

(2) Test Samples

To a drug solution of 180 mg/mL satralizumab, 20 mmol/L L-histidine/L-aspartate buffer, and 150 mmol/L L-arginine with a pH of 6.0, silicone oil was added to concentration of 0.1 mg/mL, and then Poloxamer 188, as a surfactant, was added to concentrations of 0.005 mg/mL, 0.055 mg/mL, 0.205 mg/mL, and 0.505 mg/mL. 10 mL vials were filled with 3 mL each of the prepared drug solutions, and these filled drug solutions were allowed to stand in a thermostatic chamber at 5° C. for 3 days, 1, 2, 4, or 8 weeks.

(3) Method of Evaluating Insoluble Visible Particles in Test Samples

The method described in Example 4-1 was followed.

(4) Result

The results obtained are shown in Table 11.

TABLE 11

| Poloxamer 188 concentration | | 0.005 mg/mL | 0.055 mg/mL | 0.205 mg/ml | 0.505 mg/mL |
|---|---|---|---|---|---|
| Number of insoluble visible particles/ evaluated vial number | Initial | ≥4/1 | 0/1 | 0/2 | 0/2 |
| | 3 days | ≥4/1 | 2/1 | 0/2 | 0/2 |
| | 1 W | ≥4/1 | ≥4/1 | 0/2 | 0/2 |
| | 2 W | ≥4/1 | ≥4/1 | 0/2 | 0/2 |
| | 4 W | ≥4/1 | ≥4/1 | 0/2 | 0/2 |
| | 8 W | ≥4/1 | ≥4/1 | 0/2 | 0/2 |

As is clear from Table 11, it was shown that the addition of Poloxamer 188 at 0.205 mg/mL or more suppressed the generation of insoluble visible particles.

23 24

[Example 5] Stability Test Results of a Commercial Formulation

[5-1] Stability Evaluation of Satralizumab Formulations Under Recommended Conditions and Accelerated Conditions
(1) Material
The antibody described in Example 1-1 was used.
(2) Test Samples
Drug solutions prepared with 120 mg/mL satralizumab, 20 mmol/L L-histidine/L-aspartate buffer, 150 mmol/L L-arginine, and 0.5 mg/mL Poloxamer 188 with a pH of 6.0 were left to stand in a thermostatic chamber at 25° C. for 1, 3, and 6 months. These and those that had been left to stand for 3, 6, 9, 12, 15, 18, 24, and 30 months in a thermostatic chamber at 2 to 8° C. were used as test samples.
(3) Method of Measuring Aggregate Mass of Satralizumab
Aggregate mass of the samples was measured by size exclusion chromatography (SEC) performed at a flow rate of 0.5 mL/min using a column (Tosoh, TSK Gel G3000SW×L) and a phosphate buffer solution with a pH of 7.0 for the mobile phase.
Of the peaks detected, the one with the largest area and height were taken as monomers, and peaks detected before the monomers were collectively taken as aggregates (HMWS).
The area was calculated for all peaks, and the peak area ratio of the target peak was calculated according to the following formula.

Peak area ratio of the target peak (%) =

$$\frac{\text{Peak area of the target peak}}{\text{Peak area of the target peak} + \text{Total of other peak areas}} \times 100$$

(4) Result
The results obtained are shown in Table 12.

TABLE 12

|  |  | Stored at 25° C. | Stored at 5° C. |
|---|---|---|---|
| HMWS | Initial | 0.4 | 0.4 |
| (%) | 1M | 0.6 | NT |
|  | 3M | 0.7 | 0.5 |
|  | 6M | 0.9 | 0.5 |
|  | 9M | NT | 0.6 |
|  | 12M | NT | 0.6 |
|  | 15M | NT | 0.6 |
|  | 18M | NT | 0.6 |
|  | 24M | NT | 0.7 |
|  | 30M | NT | 0.8 |

NT: Not tested

As is clear from Table 12, HMWS was 0.9% and 0.8% when stored for 6 months under accelerated conditions and 30 months under recommended storage conditions, respectively, showing a good aggregate suppression effect.

INDUSTRIAL APPLICABILITY

The formulations of the present invention are highly stable formulations that exhibit a high aggregate suppression effect in severe tests, accelerated tests, freeze-thaw tests, and long-term storage tests under recommended storage conditions. In addition, the formulations of the present invention are characterized in that foreign matter generation is suppressed for a long period of time despite containing a high concentration of an antibody (satralizumab: SA237), and are useful for the treatment of IL-6-related diseases such as neuromyelitis optica spectrum disorder (NMOSD) by subcutaneous administration.

The invention claimed is:

1. An antibody solution formulation comprising:

50 to 250 mg/mL of an antibody comprising a heavy chain variable region that comprises a CDR1 comprising the sequence of SEQ ID NO: 1, a CDR2 comprising the sequence of SEQ ID NO: 2, and a CDR3 comprising the sequence of SEQ ID NO: 3, and a light chain variable region that comprises a CDR1 comprising the sequence of SEQ ID NO: 4, a CDR2 comprising the sequence of SEQ ID NO: 5, and a CDR3 comprising the sequence of SEQ ID NO: 6;

10 to 100 mM of histidine-aspartate buffer or histidine-glutamate buffer;

0.2 mg/mL to 0.5 mg/mL of Poloxamer 188; and 5 mM to 300 mM of arginine, wherein the pH of the formulation is in the range of 5.5 to 6.6.

2. The formulation according to claim 1, which is a solution formulation that is not a reconstituted solution of a lyophilized formulation.

3. A lyophilized formulation that is a composition resulting from lyophilizing a solution comprising:

50 to 250 mg/mL of an antibody comprising a heavy chain variable region that comprises a CDR1 comprising the sequence of SEQ ID NO: 1, a CDR2 comprising the sequence of SEQ ID NO: 2, and a CDR3 comprising the sequence of SEQ ID NO: 3, and a light chain variable region that comprises a CDR1 comprising the sequence of SEQ ID NO: 4, a CDR2 comprising the sequence of SEQ ID NO: 5, and a CDR3 comprising the sequence of SEQ ID NO: 6;

10 to 100 mM of histidine-aspartate buffer or histidine-glutamate buffer;

0.2 mg/mL to 0.5 mg/mL of Poloxamer 188; and 5 mM to 300 mM of arginine, wherein the pH of the formulation after reconstitution in water is in the range of 5.5 to 6.6.

4. The formulation according to claim 1, which is free of sugars.

5. The formulation according to claim 1, wherein antibody association is suppressed.

6. A formulation for injection comprising:

(i) a container, and (ii) in the container, an antibody solution formulation that comprises, per 1 mL of solution, 50 to 250 mg of an antibody comprising a heavy chain variable region that comprises a CDR1 comprising the sequence of SEQ ID NO: 1, a CDR2 comprising the sequence of SEQ ID NO: 2, and a CDR3 comprising the sequence of SEQ ID NO: 3, and a light chain variable region that comprises a CDR1 comprising the sequence of SEQ ID NO: 4, a CDR2 comprising the sequence of SEQ ID NO: 5, and a CDR3 comprising the sequence of SEQ ID NO: 6;

0.9 to 52.3 mg of L-arginine;

1.6 to 15.5 mg of L-histidine;

0.2 mg to 0.5 mg of Poloxamer 188; and

L-aspartic acid or L-glutamic acid, wherein the pH of the solution formulation is in the range of 5.5 to 6.6.

7. A formulation for injection comprising:

(i) a container, and (ii) in the container, an antibody solution formulation that comprises, per 1 mL of solution, 60 to 200 mg of an antibody comprising a heavy chain variable region that comprises a CDR1 comprising the sequence of SEQ ID NO: 1, a CDR2 comprising the sequence of SEQ ID NO: 2, and a CDR3 comprising the sequence of SEQ ID NO: 3, and a light chain variable region that comprises a CDR1 comprising the sequence of SEQ ID NO: 4, a CDR2 comprising the sequence of SEQ ID NO: 5, and a CDR3 comprising the sequence of SEQ ID NO: 6;

8.7 to 26.1 mg of L-arginine;

1.6 to 6.2 mg of L-histidine;

0.2 mg to 1.0 mg of Poloxamer 188; and

L-aspartic acid or L-glutamic acid, wherein the pH of the solution formulation is in the range of 5.5-6.3.

8. A formulation for injection, comprising:

(i) a container, and (ii) in the container, an antibody solution formulation that comprises, per 1 mL of solution, 120 mg of an antibody comprising a heavy chain variable region that comprises a CDR1 comprising the sequence of SEQ ID NO: 1, a CDR2 comprising the sequence of SEQ ID NO: 2, and a CDR3 comprising the sequence of SEQ ID NO: 3, and a light chain variable region that comprises a CDR1 comprising the sequence of SEQ ID NO: 4, a CDR2 comprising the sequence of SEQ ID NO: 5, and a CDR3 comprising the sequence of SEQ ID NO: 6;

26.1 mg of L-arginine;

3.1 mg of L-histidine;

0.5 mg of Poloxamer 188; and

L-aspartic acid or L-glutamic acid, wherein the solution formulation has a pH in the range of 5.8-6.2.

9. The formulation according to claim 1, wherein the antibody comprises a heavy chain comprising the sequence of SEQ ID NO: 10 and a light chain comprising the sequence of SEQ ID NO: 9.

10. The formulation according to claim 1, which is for subcutaneous administration.

11. The formulation according to claim 1, which is stable at 5° C. for at least 6 months.

12. The formulation according to claim 1, wherein the proportion of aggregates at 5° C. is 2.0% or less for at least 6 months.

13. A method of suppressing antibody association and the generation of insoluble visible particles, wherein the method comprises:

adding L-aspartic acid or L-glutamic acid to a solution comprising the antibody, adding arginine to the solution such that the arginine concentration in the solution becomes 5 mM to 300 mM, and adding Poloxamer 188 to the solution such that the Poloxamer 188 concentration in the solution becomes 0.2 mg/mL to 2.0 mg/mL, wherein the antibody comprises a heavy chain variable region that comprises a CDR1 comprising the sequence of SEQ ID NO: 1, a CDR2 comprising the sequence of SEQ ID NO: 2, and a CDR3 comprising the sequence of SEQ ID NO: 3, and a light chain variable region that comprises a CDR1 comprising the sequence of SEQ ID NO: 4, a CDR2 comprising the sequence of SEQ ID NO: 5, and a CDR3 comprising the sequence of SEQ ID NO: 6.

14. The formulation according to claim 1, wherein the proportion of aggregates at 5° C. is 0.8% or less for at least 30 months.

15. The formulation according to claim 2, which is free of sugars.

16. The formulation according to claim 3, which is free of sugars.

17. The formulation according to claim 3, wherein the antibody comprises a heavy chain comprising the sequence of SEQ ID NO: 10 and a light chain comprising the sequence of SEQ ID NO: 9.

18. The formulation according to claim 6, wherein the antibody comprises a heavy chain comprising the sequence of SEQ ID NO: 10 and a light chain comprising the sequence of SEQ ID NO: 9.

19. The formulation according to claim 7, wherein the antibody comprises a heavy chain comprising the sequence of SEQ ID NO: 10 and a light chain comprising the sequence of SEQ ID NO: 9.

20. The formulation according to claim 8, wherein the antibody comprises a heavy chain comprising the sequence of SEQ ID NO: 10 and a light chain comprising the sequence of SEQ ID NO: 9.

21. The formulation according to claim 1, wherein the formulation does not contain trehalose.

22. The formulation of claim 1, wherein the formulation comprises 10 to 100 mM histidine-aspartate buffer.

23. The formulation of claim 1, wherein the formulation comprises 20 mM histidine-aspartate buffer and 150 mM arginine, and the pH of the formulation is 6.0.

24. The formulation of claim 1, wherein the formulation comprises 120 mg/mL of the antibody, 20 mM histidine-aspartate buffer, and 150 mM arginine, and the pH of the formulation is 6.0.

25. The formulation of claim 1, wherein generation of insoluble visible particles in the formulation is decreased, as compared to in an otherwise-identical formulation that comprises polysorbate 80 instead of poloxamer 188.

26. The formulation of claim 8, wherein the pH of the formulation is 6.0.

* * * * *

```
SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: An artificially synthesized sequence

<400> SEQUENCE: 1

His Asp His Ala Trp Ser
1               5

<210> SEQ ID NO 2
<211> LENGTH: 16
<212> TYPE: PRT
<213> ORGANISM: Artificial Sequence
<220> FEATURE:
<223> OTHER INFORMATION: An artificially synthesized sequence

<400> SEQUENCE: 2

Phe Ile Ser Tyr Ser Gly Ile Thr Asn Tyr Asn Pro Ser Leu Gln Gly
1               5                   10                  15

<210> SEQ ID NO 3
<211> LENGTH: 10
<212> TYPE: PRT
```

```
<213> ORGANISM: Artificial Sequence
<220> FEATURE:
<223> OTHER INFORMATION: An artificially synthesized sequence

<400> SEQUENCE: 3

Ser Leu Ala Arg Thr Thr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 4

Gln Ala Ser Thr Asp Ile Ser Ser His Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 5

Tyr Gly Ser His Leu Leu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: An artificially synthesized sequence

<400> SEQUENCE: 6

Gly Gln Gly Asn Arg Leu Pro Tyr Thr
1               5

<210> SEQ ID NO 7
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 7

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105
```

<210> SEQ ID NO 8
<211> LENGTH: 119
<212> TYPE: PRT
<213> ORGANISM: Artificial Sequence
<220> FEATURE:
<223> OTHER INFORMATION: An artificially synthesized sequence

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 9
<211> LENGTH: 214
<212> TYPE: PRT
<213> ORGANISM: Artificial Sequence
<220> FEATURE:
<223> OTHER INFORMATION: An artificially synthesized sequence

<400> SEQUENCE: 9

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 443
<212> TYPE: PRT
<213> ORGANISM: Artificial Sequence
<220> FEATURE:
<223> OTHER INFORMATION: An artificially synthesized sequence

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335
```

-continued

```
Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
            435                 440
```